(12) United States Patent
Doguet et al.

(10) Patent No.: US 12,220,572 B2
(45) Date of Patent: Feb. 11, 2025

(54) CUFF ELECTRODE OR OPTRODE COMPRISING A HANDLING FLAP

(71) Applicant: Synergia Medical, Mont-Saint-Guibert (BE)

(72) Inventors: Pascal Doguet, Mont-Saint-Guibert (BE); Marie Dautrebande, Mont-Saint-Guibert (BE); Catherine Leonard, Mont-Saint-Guibert (BE); Carmen Godfraind, Mont-Saint-Guibert (BE); Aurore Nieuwenhuys, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 715 days.

(21) Appl. No.: 17/425,750

(22) PCT Filed: Mar. 11, 2019

(86) PCT No.: PCT/EP2019/056051
§ 371 (c)(1),
(2) Date: Jul. 26, 2021

(87) PCT Pub. No.: WO2020/182293
PCT Pub. Date: Sep. 17, 2020

(65) Prior Publication Data
US 2022/0296885 A1   Sep. 22, 2022

(51) Int. Cl.
*A61N 1/05* (2006.01)
*A61B 5/24* (2021.01)
(52) U.S. Cl.
CPC .............. *A61N 1/0556* (2013.01); *A61B 5/24* (2021.01)

(58) Field of Classification Search
None
See application file for complete search history.

(56) References Cited

U.S. PATENT DOCUMENTS

| 4,602,624 A | 7/1986 | Naples et al. |
| 8,155,757 B1 * | 4/2012 | Neisz ................. A61N 1/0556 607/118 |
| 11,318,301 B2 * | 5/2022 | Doguet ............... B32B 38/0012 |
| 2003/0040785 A1 | 2/2003 | Maschino et al. |

(Continued)

FOREIGN PATENT DOCUMENTS

| DE | 102016103597 A1 | 8/2017 |
| EP | 3159036 A1 | 4/2017 |

OTHER PUBLICATIONS

Int'l Search Report for PCT/EP2019/056051, dated Jul. 31, 2019.

*Primary Examiner* — Amanda K Hulbert
(74) *Attorney, Agent, or Firm* — MaxGoLaw PLLC

(57) ABSTRACT

An implantable cuff electrode and/or optrode adapted to encircle a substantially cylindrical body tissue, and selected among self sizing cuff and a split cylinder cuff, is provided and includes
a support sheet rolled about a longitudinal axis to form a cuff electrode/optrode, with an inner handling flap provided that includes
a coupled end belonging to a coupled portion which is fixed to a portion of the outer surface of the support sheet which is adjacent to the inner edge, and
a free end, opposite the coupled end belonging to a free portion adjacent to the coupled portion and separated therefrom by a transition line, said free portion being loose from the outer surface of the support sheet.

16 Claims, 9 Drawing Sheets

(56) References Cited

U.S. PATENT DOCUMENTS

| | | |
|---|---|---|
| 2010/0233226 A1 | 9/2010 | Ferain et al. |
| 2010/0241195 A1* | 9/2010 | Meadows ............ A61N 1/3787 607/2 |
| 2012/0277819 A1 | 11/2012 | Cowley et al. |
| 2014/0188202 A1* | 7/2014 | Zarembo ............ A61N 1/0556 607/118 |
| 2015/0174396 A1 | 6/2015 | Fisher et al. |
| 2015/0374975 A1 | 12/2015 | Callegari et al. |
| 2016/0263376 A1 | 9/2016 | Yoo et al. |
| 2017/0080244 A1 | 3/2017 | Chiel et al. |
| 2017/0246453 A1 | 8/2017 | Fisher et al. |
| 2017/0304614 A1 | 10/2017 | Yoo et al. |
| 2018/0055564 A1* | 3/2018 | Clark ................. A61N 1/36053 |
| 2018/0304071 A1 | 10/2018 | Mevel et al. |
| 2019/0060641 A1 | 2/2019 | Schuttler et al. |

\* cited by examiner

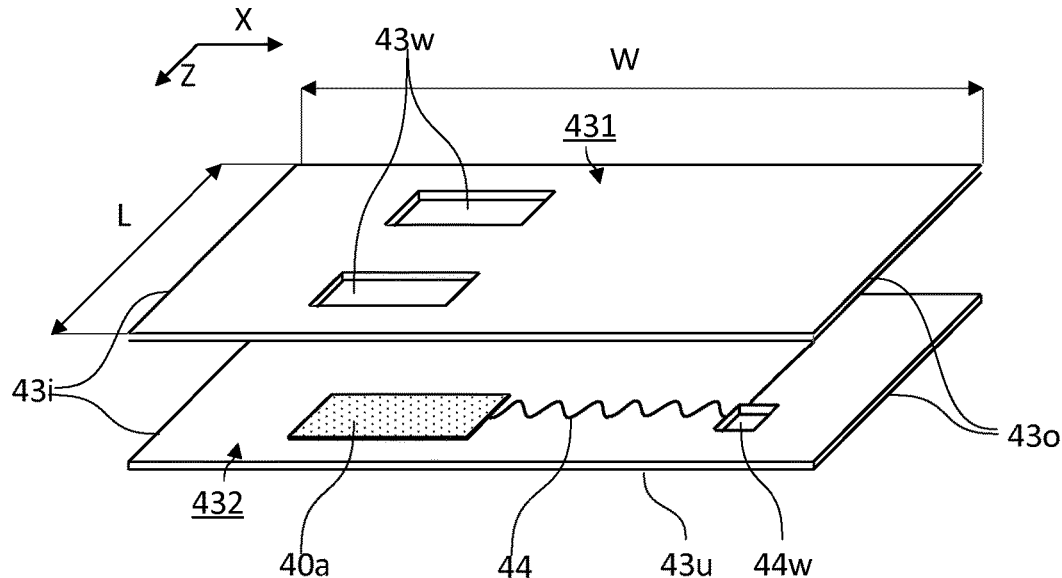
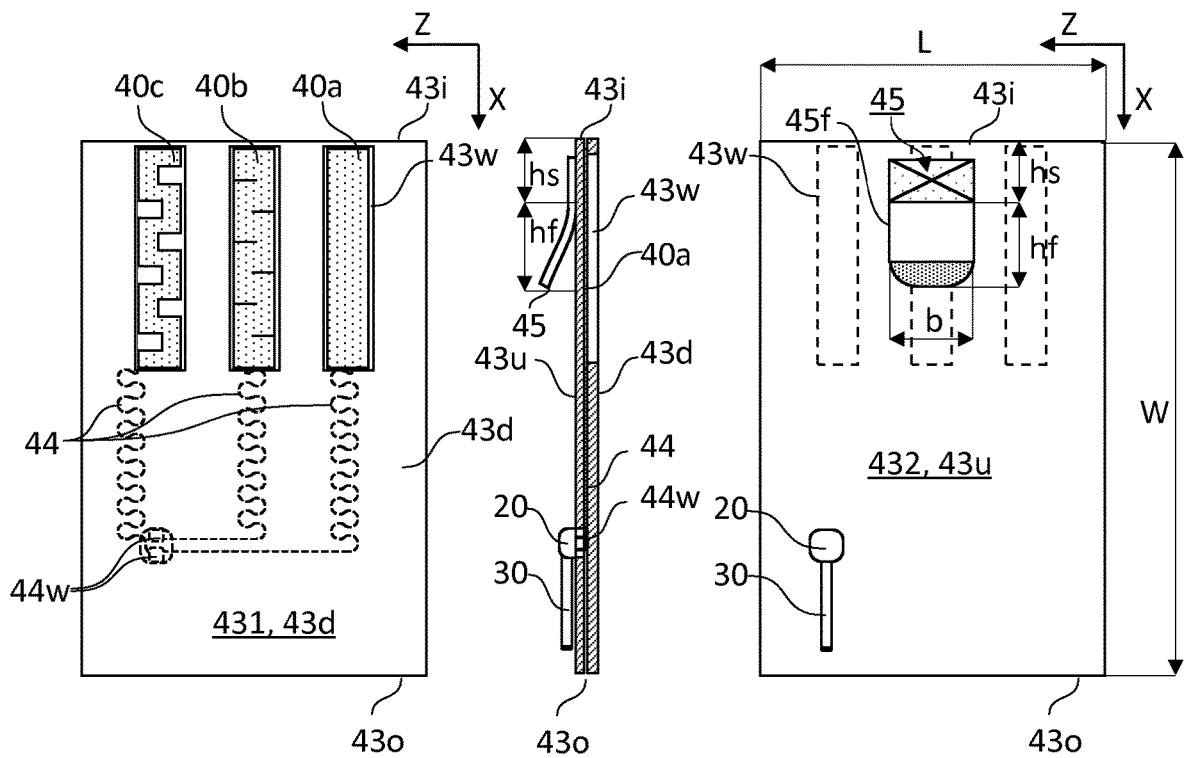
FIG.4(a)
FIG.4(b)    FIG.4(c)    FIG.4(d)

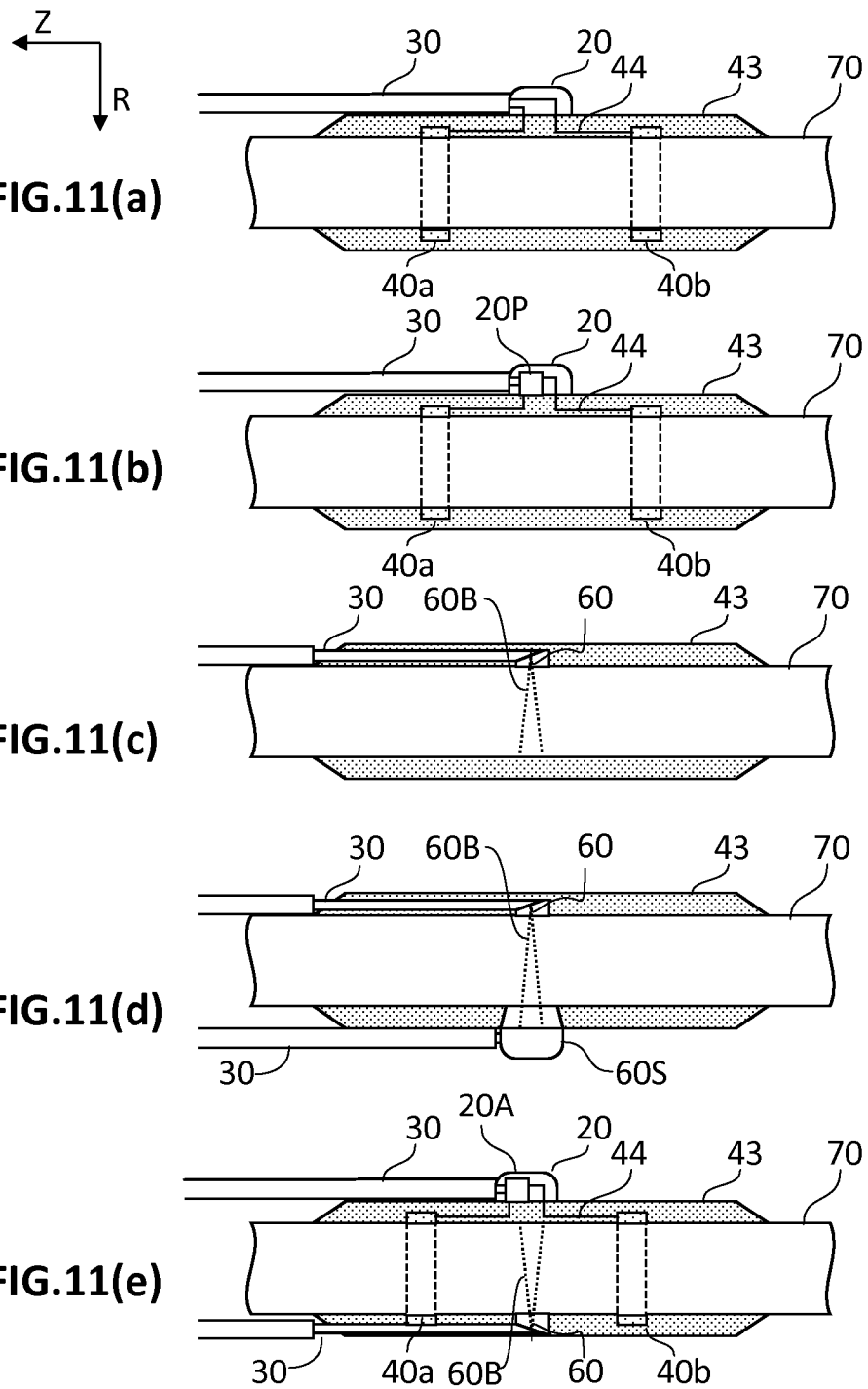

CUFF ELECTRODE OR OPTRODE COMPRISING A HANDLING FLAP

TECHNICAL FIELD

The present invention is in the field of implantable medical devices (IMD) for use in medical treatments involving the transmission of electrical pulses or light pulses between the IMD and a biological tissue. In particular, it concerns a novel concept of cuff electrodes or optrodes for coupling to a nerve or other substantially cylindrical tissue by wrapping around the nerve or tissue, which facilitates the operation of coupling the cuff-electrode to the substantially cylindrical tissue by a surgeon. It also decreases the risk of damaging sensitive components of the cuff electrode/optrode upon handling the cuff electrode/optrode during an implantation operation. These advantages can be achieved without increasing the production costs of the cuff electrode compared with state of the art cuff electrodes and shorten the duration of the implantation operation.

BACKGROUND OF THE INVENTION

Implantable medical devices (IMD) have been used for decades for treating a number of disorders, in particular neurological disorders. A major type of IMD's consists of neurostimulators, which deliver electrical pulses to a tissue such as a nerve or a muscle for diagnosing or treating a number of disorders such as Parkinson's disease, epilepsy, chronic pain, motor disorders, and many other applications. In recent years, treatment of tissues with optical energy has shown encouraging potential for the treatment of disorders, either to support the field of optogenetics or using direct infrared light. As illustrated in FIG. 1(a), in its simplest form, a device for delivering electrical pulses comprises an energy pulse generator lodged in a housing (50), stimulating electrode contacts (40a, 40b), and leads (30) coupling the electrode contacts to the energy pulse generator to transmit energy from the energy pulse generator to the electrode (40) in the form of electrical energy. The energy pulse generator can generate electrical pulses transmitted to the electrode contacts by conductive leads. Alternatively, and as described, e.g., in EP3113838B1, the energy pulse generator can generate light transmitted through optical fibres to photovoltaic cells which transform the light energy into electrical energy which is fed to the electrode contacts. The term "lead" is herein used to define both electric conductors (e.g., wires, tapes) and optical fibres.

For light treatment of a tissue, a so-called optrode can be used. An optrode can be a light emitter focusing a light beam onto a precise area of a tissue, or it can be a light sensor, sensing a reflected, transmitted, or scattered light beam emitted by a light emitter. A light emitter can be in the form of a beveled edge fibre optic or of a fibre optic coupled to a lens, focusing a light beam on a precise area of a tissue to be treated. Alternatively, the light emitter can be one or more light emitting sources, such as a light emitting diode (LED), a vertical-cavity surface-emitting laser (VCSEL), or another type of laser diode. The light emitting source can be powered by electric current in a similar way to the electrodes discussed supra.

In many applications, the electrodes or optrodes must be applied directly onto the tissue to be treated, requiring the use of an implantable device. For tissues having a substantially cylindrical configuration, cuff electrodes and/or optrodes (40) are generally used to wrap around the cylindrical tissue, such as nerves, muscular tissues, and any tissue in the shape of elongated strands or trunks. A cuff electrode comprises, on the one hand, an electrically insulating support sheet (43) comprising a sheet forming a hollow tubular support, of generally cylindrical geometry; and, on the other hand, at least one electrode contact (40a, 40b) or an optical contact (60) exposed at an inner surface of the electrically insulating support sheet, so that it is in electrical and/or optical contact with the tissue the cuff is wrapped around. The at least one electrical contact or optical contact is activated by the energy pulse generator as described above.

Electrode contacts can be for example printed onto a surface of the electrically insulating support sheet.

Three main families of cuffs are available on the market:

Self-sizing cuff (sometimes referred to as self-sizing spiral cuff or self-curling cuff) (cf. FIGS. 1(b) and 5 to 7), wherein the electrically insulating support sheet is made of a resilient material which is biased to spontaneously curl up around a cylindrical tissue. Self-sizing or self-curling cuff electrodes are particularly advantageous because their inner diameter (Dc) can vary depending on the diameter of the tissue they are wrapped around, or on variations of the diameter of the cylindrical tissue, following e.g., post-surgical inflammation or the like. Self-sizing cuff electrodes are described e.g., in U.S. Pat. No. 4,602,624.

Split-cylinder cuff (cf. FIG. 8), wherein the electrically insulating support sheet forms a cylinder with an open slit allowing insertion thereof over a cylindrical tissue. The slit is then closed. The split-cylinder cuff electrode is either provided with self-locking means or can be closed with external means, such as by ligaturing and the like. A flap may cover the slit. One drawback of split-cylinder cuff electrodes is that, once the slit is closed, the inner diameter (Dc) thereof cannot vary anymore. Examples of split-cylinder cuff electrodes can be found e.g., in U.S. Pat. No. 8,155,757. In some embodiments, the support sheet of a split-cylinder cuff electrode/optrode can be biased to spontaneously curl up around a cylindrical tissue and bring the edges of the support sheet forming the lips of the split closer together to at least partially close the split required for wrapping the support sheet around the substantially cylindrical tissue.

Helical cuff (not shown), wherein the electrically insulating support forms a helix wrapped around the cylindrical tissue. This geometry is very versatile, and several short helical cuffs can be positioned side by side at different distances, and their inner diameter can follow variations of the tissue diameter. Examples of helical cuff electrodes can be found e.g., in U.S. Pat. Nos. 5,964,702 or 8,478,428.

The present invention concerns particularly self-sizing cuff electrodes (cf. FIGS. 2, 5-7) and split-cylinder cuff electrodes (cf. FIG. 8).

One major issue with cuff electrodes concerns the implantation of a cuff electrode around a cylindrical tissue. In practice, a surgeon opens the support sheet and wraps it around a tissue to be treated. Handling of the cuff electrode is carried out by holding two opposite ends of the support sheet with tweezers, generally metallic. This operation can damage the delicate electrode contacts, which are generally printed on the support sheet, or misalign an optrode, which would render the whole implantation operation obsolete and useless.

Another potential problem with the implantation of self-sizing cuff electrodes may occur when the support sheet spontaneously curls in the wrong direction. A self-sizing cuff electrode must be wrapped with a number of N>1 loops over a cylindrical tissue, with an inner edge designed to be in contact with, and to extend parallel to the cylindrical tissue and an outer edge, opposite the inner edge, and designed to be positioned at the outer surface of the cuff electrode. The electrodes or optrodes are positioned such that they face a surface of the tissue when the support sheet is coiled around the tissue. They must be located not further than $\pi Dc$ from the inner edge, wherein Dc is the inner diameter of the cylindrical cuff electrode and is equal to the diameter of the cylindrical tissue, since the diameter Dc of a self-sizing cuff electrodes adapts to the diameter of the cylindrical tissue it is wrapped around. A wrong handling of the cuff electrode, however, which may easily happen in view of the small size thereof, may lead to the support sheet curling in the wrong direction, with the outer edge being brought into contact with the tissue and the inner edge being erroneously located at the outer surface. If this happens, the electrodes and/or optrodes would not face or only partially face the surface of the cylindrical tissue, rendering useless the implant.

PCT/EP2018/082703 proposes providing handling flaps protruding out of a perimeter of the support sheet. For examples, in case of a quadrilateral sheet, four handling flaps can be positioned at each corner of the support sheet and protruding out along a longitudinal axis (Z). When the handling flaps do prevent damaging the electrode contacts or optrodes with tweezers during handling of the cuff electrode, it is difficult to handle it properly as it requires being held at four different points at the same time. Because of the limited size of the implantation area and to limit the invasive nature of the operation, handling a cuff electrode with four tweezers may in some cases not be viable.

It can be seen from the foregoing that improvements are needed for increasing the success rate of implantation of a cuff electrode in a patient, reducing the duration of the implantation operation, and preventing both damaging the electrode and avoiding wrapping the support sheet in the wrong direction. These and other advantages are described in more details in the following sections.

SUMMARY OF THE INVENTION

The present invention is defined in the appended independent claims. Preferred embodiments are defined in the dependent claims. In particular, the present invention concerns an implantable cuff electrode and/or optrode adapted to encircle a substantially cylindrical tissue. The cuff electrode and/or optrode is selected among a self-sizing cuff and a split-cylinder cuff and comprises a support sheet and at least a first energy transfer unit.

The support sheet is non-conductive and has
an inner surface and an outer surface separated from the inner surface by a thickness,
a perimeter inscribed in an inscribing rectangle of length (L) measured parallel to a longitudinal axis (Z), and of width (W) measured parallel to a transverse axis (X) normal to the longitudinal axis (Z), the perimeter being defined by an inner edge and an outer edge extending along the length (L) of the inscribing rectangle, and by a first and second lateral edges extending along the width (W) of the inscribing rectangle.

The support sheet is rolled about the longitudinal axis (Z), forming a cuff of substantially cylindrical geometry extending over the length (L), along the longitudinal axis (Z), such that at least a portion of the inner surface forms an interior of the cuff, and such that at least a portion of the outer surface forms an exterior of the cuff.

The at least first energy transfer unit includes an electrode contact or an optical contact, which is exposed at the inner surface of the cuff.

The support sheet is provided with an inner handling flap, which comprises
a coupled end belonging to a coupled portion which is fixed to a portion of the outer surface of the support sheet which is adjacent to the inner edge, and
a free end, opposite the coupled end, belonging to a free portion adjacent to the coupled portion and separated there from by a transition line, said free portion being loose from the outer surface of the support sheet.

In a preferred embodiment, the transition line is parallel to the longitudinal axis (Z) and the inner handling flap has a breadth measured parallel to the longitudinal axis (Z) comprised between 20 and 50% of the support sheet length (L), preferably between 25 and 40% of L, more preferably between 30 and 35% of L, and is preferably comprised between 3 and 10 mm, more preferably between 4 and 6 mm. Alternatively or concomitantly, the free portion of the inner handling flap can have a length measured parallel to the transverse axis (X) comprised between 3 and 10 mm, preferably between 4 and 6 mm. Finally, the transition line can be separated from the inner edge by a distance measured parallel to the transverse axis (X) of not more than 6 mm, preferably between 1 and 4 mm.

In a preferred embodiment, the coupled end of the inner handling flap is adjacent to the inner edge and the free end faces towards the outer edge of the support sheet. The transition line extends along the longitudinal axis (Z) and is separated from the inner edge by a distance measured parallel to the transverse axis (X) of not more than 4 mm, preferably comprised between 1 and 3 mm.

Preferably, the implantable cuff electrode comprises a first and a second electrode contacts to form a bipolar electrode. More preferably, the cuff electrode further comprises a third electrode contact to form a tripolar electrode.

The first and second electrode contacts, and preferably the third electrode contact are in the form of,
continuous strips extending parallel to the transverse axis (X) when the support sheet is deployed on a flat surface, at least along the portion of the inner surface forming the interior of the cuff, preferably in a straight line or forming a serpentine when projected on the plane (X, Z), or
discrete electrode contact elements distributed parallel to the transverse axis (X) when the support sheet is deployed on a flat surface, at least along the portion of the inner surface forming the interior of the cuff.

The support sheet can be formed of an outer sheet comprising the outer surface, adhered to an inner sheet comprising the inner surface, said inner sheet being made of a resilient material and being resiliently pre-strained along the transverse axis (X), to create a bias suitable for self-curling the support sheet about the longitudinal axis (Z), to resiliently form a substantially cylindrical cuff of inner diameter (Dc). The cuff electrode and/or optrode of the present invention is either a self-sizing cuff, or a split-cylinder cuff.

In case the implantable cuff electrode and/or optrode forms a self-sizing cuff, the support sheet can have a bias and inner and outer widths (W), such that the support sheet self-curls into the substantially cylindrical cuff of inner diameter (Dc), with N loops, with N being comprised between 1.1 and 3.5, preferably between 1.5 and 3.0, more preferably between 2.3 and 2.8, wherein the inner edge forms with the at least portion of the inner surface the interior of the cuff, and the outer edge forms with the at least portion of the outer surface the exterior of the cuff, and the at least first energy transfer unit is closer to the inner edge than to the outer edge, and preferably has a length of not more than πDc.

In case the implantable cuff electrode and/or optrode forms a split-cylinder cuff, the support sheet can have a bias and inner and outer widths (W), such that the support sheet self-curls into the substantially cylindrical cuff of inner diameter (Dc), with N loops, with N being comprised between 0.8 and 1.0, and wherein the inner edge and outer edge face each other and preferably contact each other, and wherein the at least first energy transfer unit has a length of up to W.

In addition to the inner handling flap, an outer handling flap can also be provided in a portion of the outer surface contiguous to the outer edge. The outer handling flap comprises a coupled end belonging to a coupled portion which is fixed to a portion of the outer surface of the support sheet which is adjacent, preferably contiguous to the outer edge, and a free end, opposite the coupled end, and adjacent to the outer edge of the support sheet, said free end belonging to a free portion which is loose from the outer surface of the support sheet.

In addition or in place of the outer handling flap, a central portion of the outer edge can be separated from the edge of the inscribing rectangle which is adjacent to the inner edge by the width (W) measured parallel to the transverse axis (X), and can be flanked by a first and second side portions, joining the central portion to the first and second lateral edges of the support sheet, respectively, the first and second lateral portions being separated from the inner edge by a distance shorter than the width (W). The central portion can be formed either by, a point forming an angle between the first and second side portions, or a straight or curved segment of breadth measured parallel to the longitudinal axis (Z) lower than 80% of the longitudinal length (L), preferably comprised between 5 and 50% of L, more preferably between 10 and 33% of L.

The inner edge and/or the outer edge of the insulating support sheet can be highlighted comprising one or more of a coloured area, a coloured line, an arrow, or other graphical or alpha-numerical indication applied at or adjacent to said inner and/or outer edge(s).

Alternatively, the inner handling flap can comprise a colour code. The outer handling flap can also comprise a colour code, different from the colour code of the inner handling flap.

The implantable cuff electrode and/or optrode of the present invention can be used in a method for implanting a cuff electrode and/or optrode around a tissue of substantially cylindrical geometry, the method comprising the following steps:

(a) Providing an implantable cuff electrode and/or optrode according to any one of the preceding claims, (b) Gripping the free portion of the inner handling flap with a tweezer, (c) Bringing a portion of the inner surface contiguous to the inner edge in contact with the tissue, while holding the inner handling flap with the tweezer, and (d) Wrapping the support sheet around the tissue and, after 0.8 to 1.5 loops, releasing the grip by the tweezer on the inner handling flap, The wrapping the support sheet in step (b) can be performed with a second tweezer gripping either the outer edge of the support sheet or a free end of an outer handling flap and releasing and removing the tweezer once the outer edge is in an implanted position.

BRIEF DESCRIPTION OF THE FIGURES

For a fuller understanding of the nature of the present invention, reference is made to the following detailed description taken in conjunction with the accompanying drawings in which:

FIG. 4: shows (a) a perspective exploded view of a stretched cuff electrode comprising a two-layer laminated support sheet, with electrode contacts sandwiched between an inner layer and an outer layer, (b) a front view of the inner surface of a stretched cuff electrode comprising serpentine shaped conductive tracks and electrode contacts of different geometries, (c) side view of the stretched cuff electrode of FIG. 4(b), and (d) front view of the outer surface of the stretched cuff electrode of FIG. 4(b).

FIG. 11: shows various configurations of cuff electrodes and/or cuff optrodes: (a) cuff electrode, (b) cuff electrode with electrical sensing, (c) cuff optrode with beveled fibre optic, (d) cuff optrode with optical sensing, (e) optrode with electrical sensing.

DETAILED DESCRIPTION OF THE INVENTION

Figure 1A:
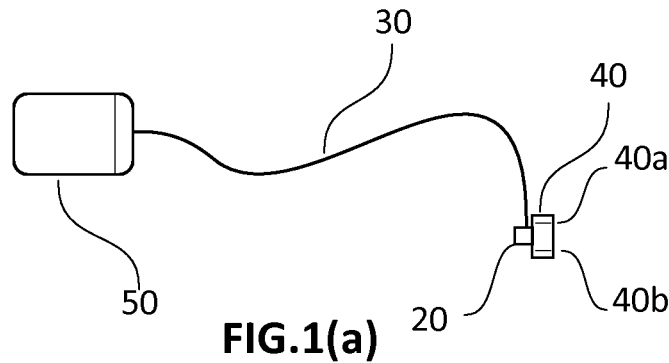
FIG. 1: shows (a) an IMD according to the present invention and (b) an example of self-sizing cuff electrode.
Figure 1B:
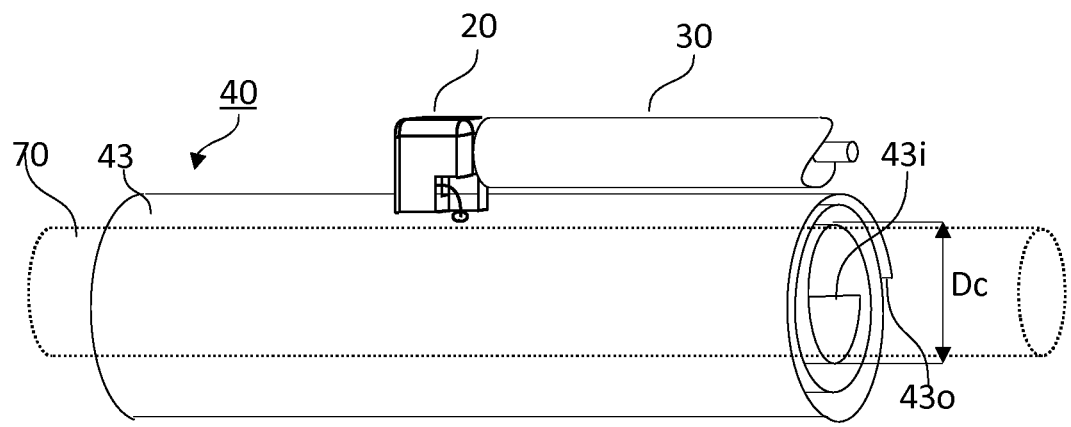

As illustrated in FIG. 1(a), an implantable cuff electrode and/or optrode according to the present invention is designed for use with an implantable medical device (IMD) comprising a housing (50) containing the electronics for controlling the functions of the IMD, including for example a source of power generally in the form of a primary or rechargeable battery, and an energy pulse generator, which can include an electrical pulse generator or a light emitting source. Because the housing (50) is usually too bulky to be implanted adjacent to the tissue to be treated, it is generally implanted in an easy to access region, remote from the tissue to be treated and from the cuff electrode/optrode. The cuff electrode/optrode (40) is therefore coupled to the housing by a lead (30) suitable for transporting the energy generated by the energy pulse generator to the electrode contacts (40a-c) or to the optrode (60) of the cuff electrode/optrode. The energy is delivered in the form of electric energy to electrode contacts and to light emitting sources, such as LED's or VCSEL's, or in the form of light energy to a beveled fibre optic or to a fibre optic coupled to a micro-optic device, such as a lens, a mirror, etc. The lead may consist of conductive leads, for use with an electrical pulse generator, conducting the electrical pulses from the generator directly to the electrode contacts or light emitting sources, without any transformation of the energy. An IMD of this kind is described e.g., in WO2009046764. Alternatively, the leads may comprise optical fibres for use with a light emitting source such as a LED. The optical energy is transported to a photovoltaic cell located adjacent to the cuff electrode/optrode, for conversion of the optical energy into electrical energy. An IMD of this kind which is suitable for use with a cuff electrode of the present invention is described e.g., in WO2016131492. Both energy transfer systems are known in the art and a person of ordinary skill in the art knows the pros and cons of each system and can select the best configuration most suitable to a given case. The present invention is not restricted to any particular energy transfer system type. The use of optical fibres with photovoltaic cells is, however, preferred for the numerous advantages it has over the use of electrical wires, such as the lack of interaction with magnetic fields encountered e.g., in magnetic resonance imaging (MRI) or in security portals at airports and the like.

As shown in FIGS. 2 to 11, a cuff electrode/optrode according to the present invention comprises an electrically non-conductive support sheet (43) in the form of a tubular cuff structure of inner diameter (Dc), comprising an inner surface (43d) and an outer surface (43u) separated from the inner surface by a thickness. The support sheet has a perimeter inscribed in an inscribing rectangle of length (L) measured parallel to a longitudinal axis (Z), and of width (W) measured parallel to a transverse axis (X) normal to the longitudinal axis (Z). The perimeter is defined by an inner edge (43i) and an outer edge (43o) extending along the length (L) of the inscribing rectangle, and by a first and second lateral edges extending along the width (W) of the inscribing rectangle.

The support sheet is rolled about the longitudinal axis (Z), forming a cuff of substantially cylindrical geometry of inner diameter (Dc) and extending over the length (L) along the longitudinal axis (Z), such that at least a portion of the inner surface (43d) forms an interior of the cuff, and such that at least a portion of the outer surface (43u) form an exterior of the cuff. The present invention concerns, on the one hand, self-sizing cuffs, which curl around and wrap a cylindrical tissue with N>1 loops and, on the other hand, split-cylinder cuffs, which curl around and wrap a cylindrical tissue with N≤1 loop.

The inner diameter (Dc) depends on the dimensions of the substantially cylindrical tissue the cuff is to be wrapped around. The support sheet (43) of self-sizing cuff electrodes/optrodes (40) is biased such as to spontaneously curl from a stretched, planar configuration to a cylindrical geometry, with more than one loop. The inner diameter of a self-sizing electrode/optrode can therefore vary with variations of the diameter of the tissue it is wrapped around.

A split cuff electrode/optrode is inserted around a tissue by enlarging the split to form a gap sufficient for inserting the tissue therethrough, and then the gap is reduced to fit the dimensions of the tissue. For electrodes, it is preferred that the slit be closed (i.e., N=1 loop) to reduce stray current losses. The support sheet (43) of a split electrode/optrode can also be biased as explained supra for self-sizing electrodes/optrodes and can thus also adapt to small variations of the dimensions of the tissue. Alternatively, the support sheet is not biased, and the cuff must be stabilized by stitching across the slit or by introducing a slit sheath around the cuff.

The inner diameter (Dc) is preferably comprised between 0.2 and 5 mm, more preferably between 1 and 3.5 mm, most preferably between 2 and 3 mm. The inner diameter (Dc) of the self-sizing cuff electrode/optrode is generally comprised between 80 and 95% of the substantially cylindrical tissue diameter (Dn) of the tissue to be treated. For split cylinder cuff electrodes/optrodes, the inner diameter (Dc) is generally equal to or slightly larger than the tissue diameter (Dn). For example, Dc can be comprised between 100 and 110% of Dn. The various components of the cuff electrode/optrode of the present invention are described in continuation.

As illustrated schematically in FIG. 11, the cuff electrode/optrode of the present invention also comprises at least a first electrode contact (40a), generally two and even three electrode contacts (40b, 40c) exposed at the inner surface of the cuff. Alternatively, or concomitantly, the tubular cuff structure comprises at least a first optical contact (60), preferably two or more optical contacts exposed at the inner surface of the cuff.

Electrically Insulating Support Sheet (43)

The cuff electrode/optrode (40) comprises an electrically insulating support sheet (43) for coupling the implantable electrode/optrode to a cylindrical tissue, such as a nerve. The support sheet (43) comprises an inner surface (43d), at least a part of which contacts the substantially cylindrical tissue around which it is wrapped, and further comprises an outer surface (43u) separated from the inner surface by a thickness of the support sheet. The support sheet has a perimeter inscribed in an inscribing rectangle of length (L) measured parallel to a longitudinal axis (Z), and of width (W) measured parallel to a transverse axis (X) normal to the longitudinal axis (Z). The perimeter is defined by an inner edge (43i) and an outer edge (43o) extending along the length (L) of the inscribing rectangle, and by a first and second lateral edges extending along the width (W) of the inscribing rectangle The support sheet is used for securing the electrode contacts (40a-c) or optical contacts (60) at their treatment positions in electrical/optical contact with the substantially cylindrical tissue to be treated for long term implantation. The support sheet also serves for confining the current as much as possible in a circuit including a first and a second electrode contacts (40a, 40b) and optionally a third electrode contact (40c) passing through the substantially cylindrical tissue located between said first and second electrode contacts.

The support sheet is made of a non-conductive material, preferably a polymer. If the insulating material must be deformed during implantation and for accommodating any body movement, for examples for self-sizing cuff electrodes (cf. FIGS. 2 and 7) and, in some cases, for split cylinder cuff electrodes (cf. FIG. 8), it is preferably made of an elastomeric polymer, such as silicone, a polyimide or polyurethane elastomer, or any biocompatible elastomer. For other electrodes geometries, such as non-resilient split cylinder cuff electrodes, besides biocompatible elastomers, the support sheet can be made of a more rigid material such as for example polyurethane or an epoxy resin.

As shown in FIGS. 3 to 9, the support sheet consists of a sheet material that is rolled up about a longitudinal axis (Z), to form a tubular, substantially cylindrical cuff structure of inner diameter (Dc), measured along a radial direction normal to the longitudinal axis (Z), and extending over a length (L) along the longitudinal axis (Z). The tubular cuff structure comprises an inner surface (43d), at least a part of which forming an interior of the cuff, and an outer surface (43u) forming an exterior of the cuff, separated from the inner surface by a thickness of the cuff. As illustrated in FIGS. 3 to 6, the perimeter of the support sheet when spread on a flat surface is inscribed in an inscribing rectangle of length (L) measured parallel to a longitudinal axis (Z), and of width (W) measured parallel to a transverse axis (X) normal to the longitudinal axis (Z). The perimeter is defined by an inner edge (43i) and an outer edge (43o) extending along the length (L) of the inscribing rectangle, and by a first and second lateral edges extending along the width (W) of the inscribing rectangle. Each of the inner and outer edges (43i, 43o), and each of the lateral edges can form a continuous line, either straight, or curved, or can form a discontinuous line formed of segments which can be either straight or curved. For example, a rectangular support sheet has four straight edges (cf. FIGS. 3, 4, and 9(a)). One or more edges can be at least partially curved (cf. outer edge (43o) of FIG. 9(b)), or discontinuous comprising various segments (cf. lateral edges of FIG. 6(a) and outer edges of FIGS. 9(c)&9(d)).

At least a portion of the inner surface of the cuff is in contact with the tissue when the cuff electrode is implanted around a substantially cylindrical tissue (70) (a substantially cylindrical tissue is herein defined as a tissue in the form of an elongated fibre, strand, trunk, etc., such as nerves, which is substantially cylindrical or at least prismatic, and having a length to diameter aspect ratio of at least 3, preferably at least 5, more preferably at least 10).

Inner Handling Flaps (45)

Figure 2A:
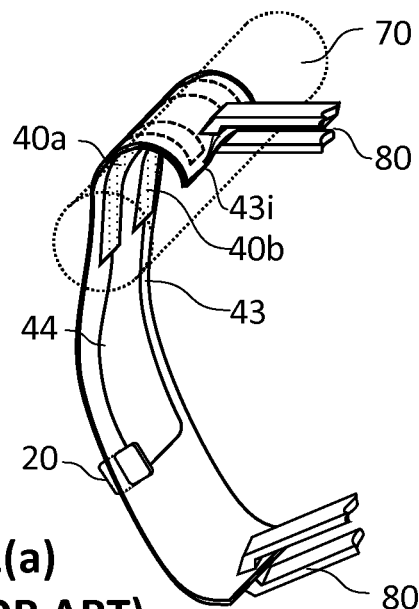
FIG. 2: shows how a cuff electrode of the prior art can be wrapped around a nerve using tweezers (a) self-sizing cuff electrode, (b) split cylinder cuff electrode, with a high risk of damaging the inner (and outer) edges of the support sheet and, in particular, the electrode contacts upon implanting the cuff electrode.
Figure 2B:
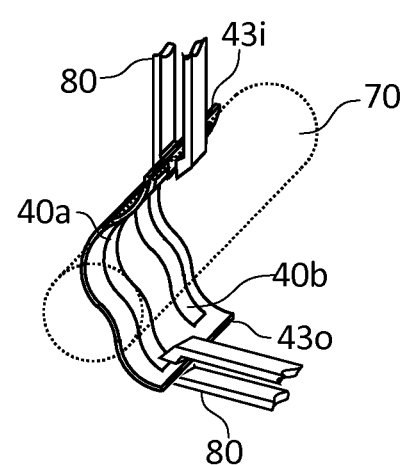

Referring to FIG. 2, a cuff electrode (40) of the prior art is implanted around a cylindrical tissue (70) by using tweezers (80) which are generally metallic. There is little alternative than to grip the support sheet (43) by the two opposite inner and outer edges (43i, 43o) to uncurl and stretch the support sheet to allow the wrapping of the tissue with the support sheet (43). By doing so, there is a high risk to contact and damage the electrode contacts (40a, 40b), with the tweezer gripping the inner edge (43i) in case of a self-sizing cuff electrode illustrated in FIG. 2(a), and with both tweezers gripping the inner and outer edges (43i, 43o) of a split cylinder cuff electrode illustrated in FIG. 2(b). The risk of damaging the electrode contacts is inadmissible as it could ruin the cuff electrode and render the whole implantation operation useless.

Figures 10A, 10B:
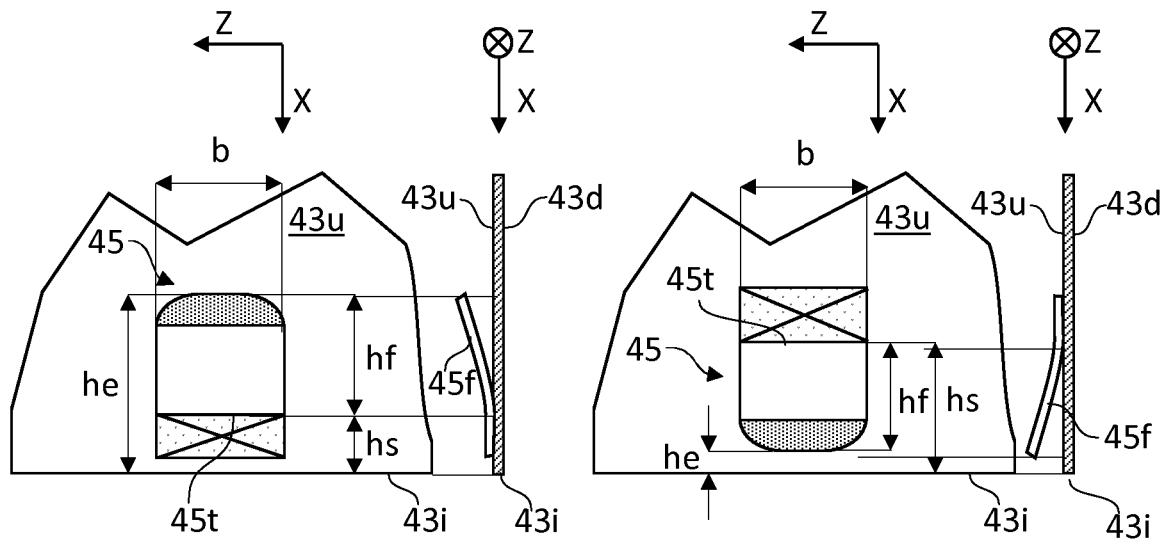
FIG. 10: shows various embodiments of inner handling flaps.
Figures 10C, 10D:
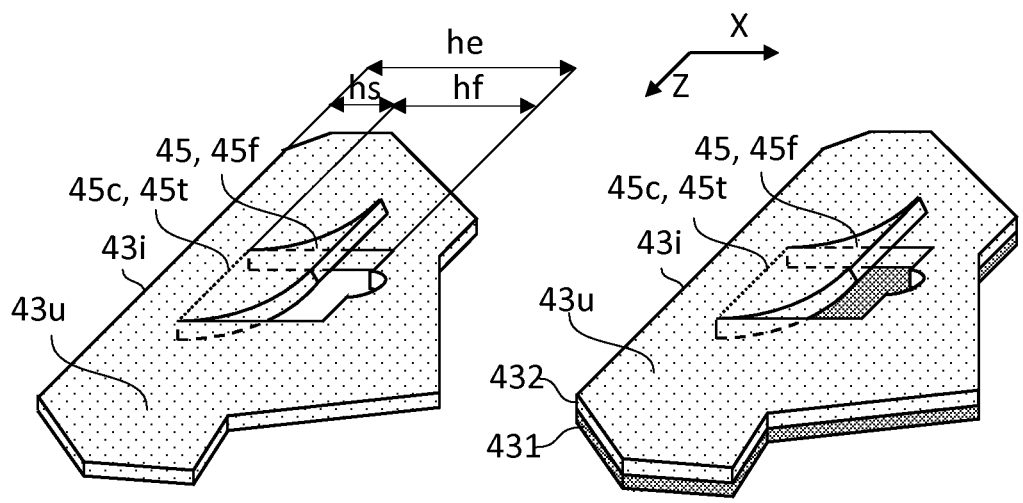

The gist of the present invention is to provide the outer surface (43u) of the support sheet (43) with an inner handling flap (45). The inner handling flap (45) comprises a coupled end belonging to a coupled portion (45c) which is fixed to a portion of the outer surface (43u) of the support sheet (43) which is adjacent to the inner edge (43i). It also comprises a free end, opposite the coupled end belonging to a free portion (45f) adjacent to the coupled portion (45c) and separated therefrom by a transition line (45t), said free portion being loose from the outer surface (43u) of the support sheet. The fixed portion can be as small as necessary to reliably couple the inner handling flap to the support sheet's outer surface. The inner handling flap can be coupled to the outer surface (43u) of the support sheet (43) by any means known to a person of ordinary skill in the art, including gluing, welding such as ultrasonic welding, laser welding, heat welding, mechanical fixing. It is also possible, as illustrated in FIG. 10(c), to cut a section of the outer surface (43u) of the support sheet defined by an open sector and pull out the thus formed inner handling flap (45) with the transition line (45t) being formed by the uncut line connecting the two ends of the cut off open sector. This option is particularly interesting when the support sheet is formed by a laminate of two layers (431, 432) as illustrated in FIG. 10(d) and as discussed below in relation with FIG. 4. A notch can be provided to allow a tip of a tweezer to access a bottom surface of the inner handling flap (45).

In a preferred embodiment, the transition line (45t) is parallel to the longitudinal axis (Z). The inner handling flap is preferably centred with respect to the inner edge (43i). The inner handling flap can have a breadth (b) measured parallel to the longitudinal axis (Z) comprised between 20 and 50% of the support sheet length (L) (i.e., the length (L) of the inscribing rectangle), preferably between 25 and 40% of L, more preferably between 30 and 35% of L. For example, the breadth (b) of the inner handling flap (45) can be comprised between 3 and 10 mm, more preferably between 4 and 6 mm.

The free portion (45f) of the inner handling flap (45) can have a length (hf) measured parallel to the transverse axis (X) comprised between 3 and 10 mm, preferably between 4 and 6 mm. The transition line (45t) is preferably located close to the inner edge (43i) to allow full opening of the cuff. This is advantageous because with the bias on the support sheet, the inner edge could curl up over the portion separating the inner edge from the transition line (45t) in case the latter was located too far apart from the inner edge. For example, the transition line can be separated from the inner edge (43i) by a distance (hs) measured parallel to the transverse axis (X) of not more than 6 mm, preferably between 1 and 4 mm. The magnitudes hf, hs, and other magnitudes defining the dimensions of an inner handling flap are illustrated in FIGS. 3(d), 4(d), and 10(a) to 10(c).

In one embodiment illustrated in FIGS. 3(c), 3(d), 4(c), 4(d), 5(a), 6(a), 7(d), 9(a)-9(c), and 10(a), 10(c), 10(d), the coupled end of the inner handling flap (45) is adjacent to the inner edge (43i) and the free end faces towards the outer edge (43o) of the support sheet (43). The transition line extends along the longitudinal axis (Z) and can be separated from the inner edge (43i) by a distance (hs) measured parallel to the transverse axis (X) of not more than 4 mm, preferably comprised between 1 and 3 mm. The free end of the inner handling flap can be separated from the inner edge (43i) by a distance (he) comprised between 4 and 11 mm, preferably between 5 and 8 mm. This embodiment is particularly suitable for, but not restricted to self-sizing cuff electrodes.

In an alternative embodiment illustrated in FIGS. 8(d)-(f), 9(d), and 10(b), the free end of the inner handling flap (45) is adjacent to the inner edge (43i) and the coupled end faces towards the outer edge (43o) of the support sheet (43). The free end of the inner handling flap can be separated from the inner edge (43i) by a distance (he) comprised between 0 and 3 mm, preferably between 0.5 and 2 mm. The transition line extends along the longitudinal axis (Z) and can be separated from the inner edge (43i) by a distance (hs) measured parallel to the transverse axis (X) comprised between 4 and 10 mm, preferably between 6 to 8 mm. This embodiment is particularly suitable for, but not restricted to split-cylinder cuff electrodes.

The free end and at least part of the free portion can be coloured in a distinguishable colour to help a surgeon to identify the free end where the inner handling flap can be gripped by tweezers without risk of damaging the electrode contacts (40a-40c) or the optical contact (60).

The cuff electrode of the present invention can also comprise an outer handling flap (46) for further facilitating handling of the cuff electrode upon implantation of the cuff electrode over or, if it applies, removal thereof from the nerve or other cylindrical tissue.

Outer Handling Flaps (46)

Figure 8A:
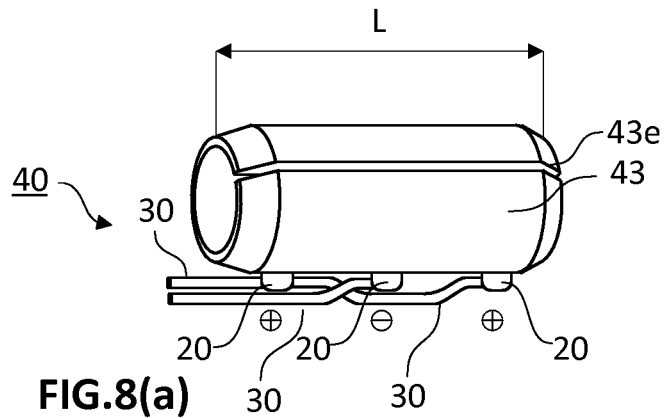
FIG. 8: shows a split-cylinder cuff electrode (a) died view, (b) front view, (c) perspective view, (d)-(f) steps for coupling the split-cylinder cuff electrode to a cylindrical tissue.
Figures 8B, 8C:
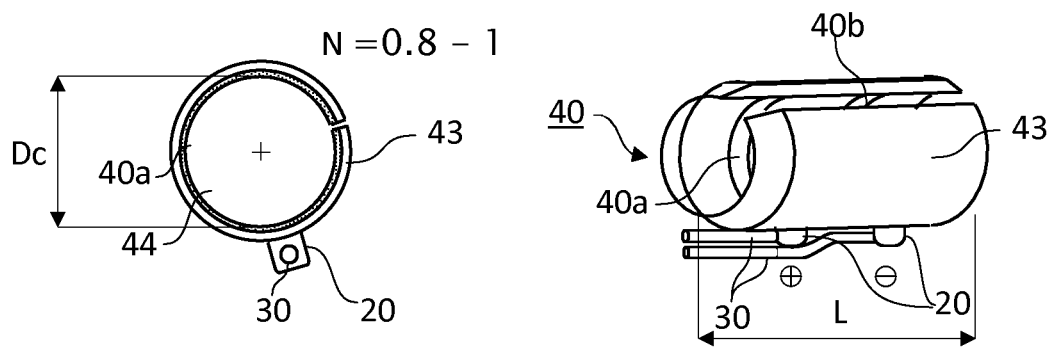
Figures 8D, 8E, 8F:
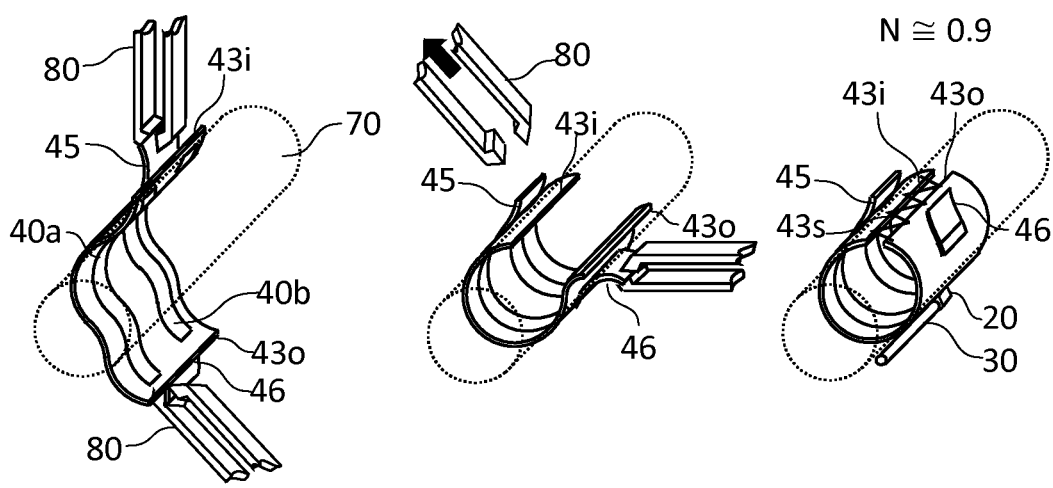
Figure 9A:
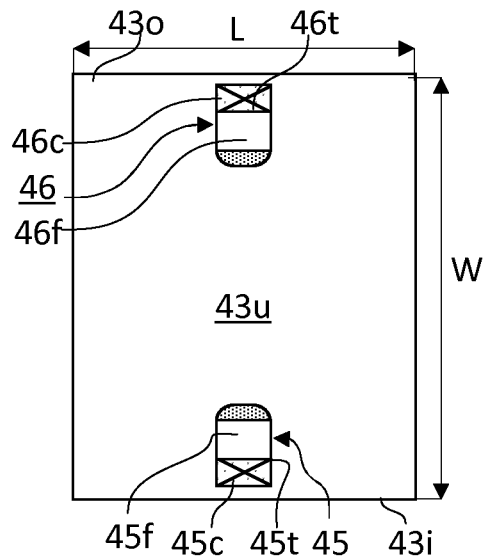
FIG. 9: shows various embodiments of support sheet geometries and handling flaps arrangements.

Examples of cuff electrodes comprising an outer handling flap (46) are illustrated in FIGS. 8(d) to 8(f), 9(a) and 9(c). An outer handling flap (46) is similar in construction and dimensions to the inner handling flap (45) discussed supra. The outer handling flap (46) is provided at a portion of the outer surface (43u) which is adjacent and contiguous to the outer edge (43o). Like the inner handling flap (45), the outer handling flap (46) is preferably centred with respect to the length (L) of the inscribing rectangle. The outer handling flap (46) comprises a coupled end belonging to a coupled portion which is fixed to a portion of the outer surface (43u) of the support sheet (43). It also comprises a free end, opposite the coupled end and belonging to a free portion adjacent to the coupled portion (46c) and separated therefrom by a transition line (46t). The transition line preferably extends along the longitudinal axis (Z). The free end of the outer handling flap (46) can be adjacent to the outer edge (43o) as illustrated in FIGS. 8(d) to 8(f) and 9(c). Alternatively, the coupled end can be adjacent to the outer edge (43o) as shown in FIG. 9(a).

The outer handling flap (46) can be coupled to the outer surface (43u) of the support sheet (43) by any means known to a person of ordinary skill in the art, including gluing, welding such as ultrasonic welding, laser welding, heat welding, mechanical fixing. It is also possible to cut a section of the outer surface (43u) of the support sheet defined by an open sector and pull out the thus formed outer handling flap (46) with the transition line (46t) being formed by the uncut line connecting the two ends of the cut off open sector, as illustrated in FIG. 10(c) for an inner handling flap (45). This option is particularly interesting when the support sheet is formed by a laminate of two layers (431, 432) as illustrated in FIG. 10(d) for an inner handling flap (45).

An outer handling flap (46) is particularly preferred for split cylinder cuff electrodes, since the electrode contacts (40a-40c) can extend over a substantial portion, or even over the whole of the width (W) of the support sheet (43), close to the outer edge (43o) thereof, and tweezers (80) gripping the outer edge (43o) of the support sheet may damage the electrode contacts.

With self-sizing cuff electrodes, the electrode contacts generally do not extend close to the outer edge (43o) of the support sheet and the risk of damaging the cuff electrode with tweezers at the outer end (43o) is reduced. An outer handling flap can nonetheless be advantageous in self-sizing cuff electrodes too for comfort of the surgeon, as it provides a firm and secure grip at a central portion adjacent to the outer edge (43o).

Two main types of support sheets (43) are discussed more in detail in continuation: self-sizing support sheets and split-cylinder support sheets.

Self-Sizing Insulating Support Sheets

Figure 3A:
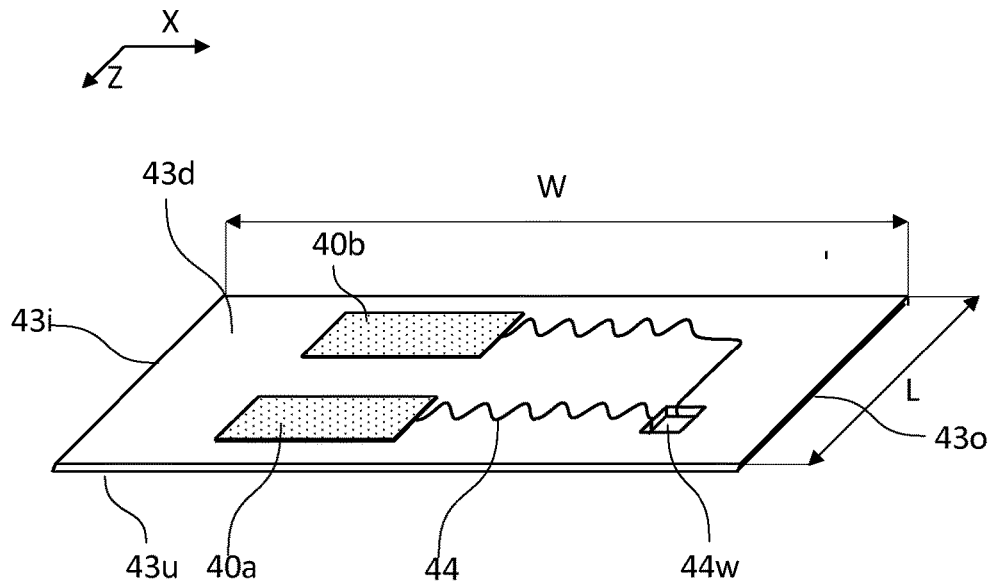
FIG. 3: shows (a) a perspective view of a stretched cuff electrode comprising a single-layer support sheet with electrode contacts applied to the inner surface, (b) a front view of the inner surface of a stretched cuff electrode comprising serpentine shaped conductive tracks and electrode contacts of different geometries, (c) side view of the stretched cuff electrode of FIG. 3(b), and (d) front view of the outer surface of the stretched cuff electrode of FIG. 3(c).
Figures 3B, 3C, 3D:
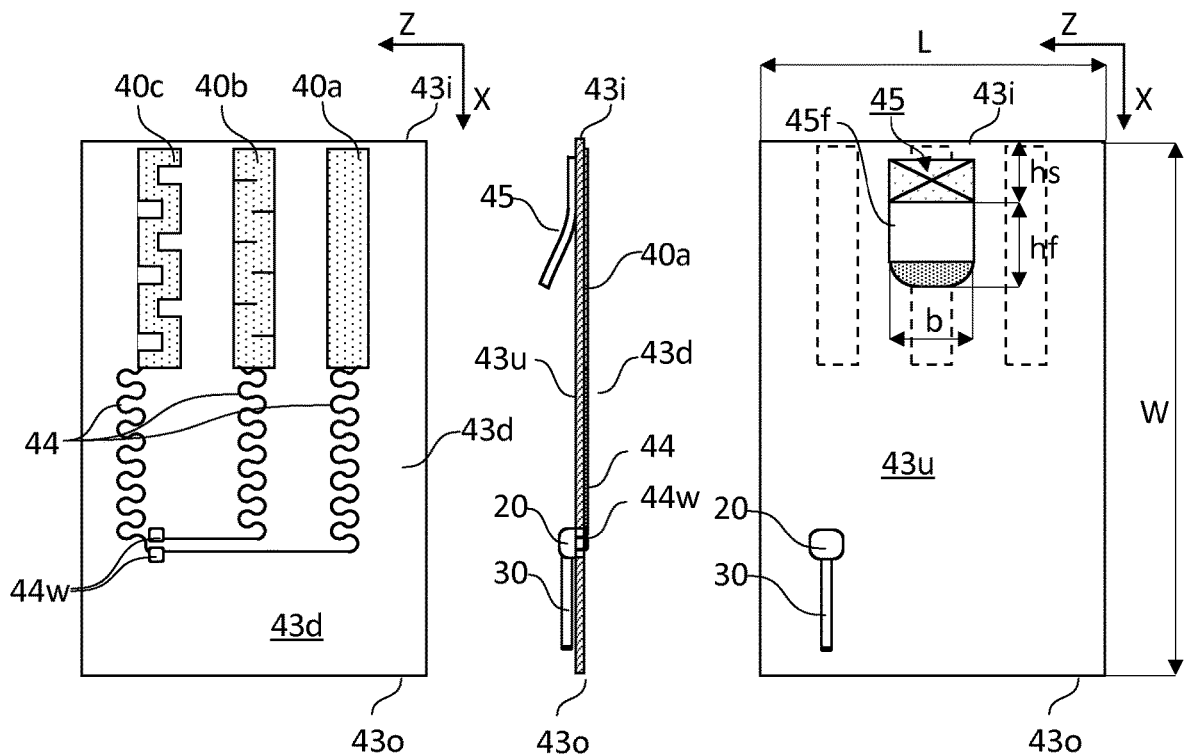

As shown in FIGS. 3(a)&3(c) and 10(c), the sheet material can be made of a single layer. Alternatively, as shown in FIGS. 4(a)&4(c) and 10(d), the sheet material can consist of a laminate comprising an inner sheet (431) comprising the inner surface (43d) and an outer sheet (432) comprising the outer surface (43u) either adhered directly to one another thus forming a two-layer laminate, or to one or more core layers, thus forming a multi-layered laminate with more than two layers. Self-sizing cuff electrodes must be biased so that the insulating sheet material spontaneously rolls up to form a tubular cuff structure. This can be achieved with a laminate comprising at least two layers. The inner layer including the inner surface (43d) is pre-stretched along the transverse axis (X) prior to and during adhesion thereof to the un-stretched outer layer including the outer surface (43u). When a laminate is formed, the force pre-stretching the inner layer is released, and the inner layer contracts back to its equilibrium dimension along the transverse axis (X), thus curling the sheet into a tubular cuff about the longitudinal axis (Z).

Because of the Poisson's ratio inherent to every material, which is the transverse to axial strain ratio of a material, by stretching the inner sheet along the transverse axis (X), the inner sheet necessarily contracts along the longitudinal axis (Z). Upon releasing the stress on the inner sheet to allow it to contract back to its equilibrium configuration along the transverse axis (X), the inner sheet also expands along the longitudinal axis (Z), and may thus form in some cases trumpet shaped cuff edges. Trumpet shaped edges are detrimental to a good contact between the tissue (70) and the electrode contacts (40a-40c) and can be responsible for current losses which are detrimental to the efficacy of the cuff electrode. This can be obviated to a certain degree by increasing the distance separating an electrode contact from a trumpet shaped edge, compared with the corresponding distance required in a straight edge cuff electrode. The cuff length along the longitudinal axis is thus increased, which is not desirable as it becomes more invasive and cumbersome to implant. To prevent trumpet edges from forming as the support sheet curls up to form a tubular cuff, it suffices to pre-stretch the inner sheet along the longitudinal axis (Z) too, by an amount corresponding to the product of the material's Poisson's ratio and the pre-stretching level of the inner sheet along the transverse axis (X). If some level of trumpet shaped edges were desired, a fraction only of the foregoing pre-stretching along the longitudinal axis (Z) could be applied instead.

In a first embodiment illustrated in FIG. 4(a), a two-layer laminate can be formed of an inner sheet (431) including the inner surface (43d) and an outer sheet (432) including the outer surface (43u) adhered to one another or to additional core layers sandwiched between the inner and outer sheets.

The bias formed by the pre-stretching of the inner sheet (431) permits the support sheet (43) to spontaneously curl and form the support of a self-sizing electrode. A self-sizing electrode forms a number N>1 loop around the tissue it is wrapped around. Generally, it is preferred that the self-sizing cuff electrode wraps a cylindrical tissue of diameter (Dc) with N loops, with N being comprised between 1.1 and 3.5, preferably between 1.5 and 3.0, more preferably between 2.3 and 2.8. When properly curled, the inner edge (43i) forms with at least a portion of the inner surface (43d) the interior of the cuff, and the outer edge (43o) forms with at least a portion of the outer surface (43u) the exterior of the cuff. The at least first energy transfer unit (40a, 60) is closer to the inner edge (43i) than to the outer edge (43o), and preferably has a length of not more than πDc (i.e. the circumference of one loop forming a circle of diameter Dc).

Figure 5A:
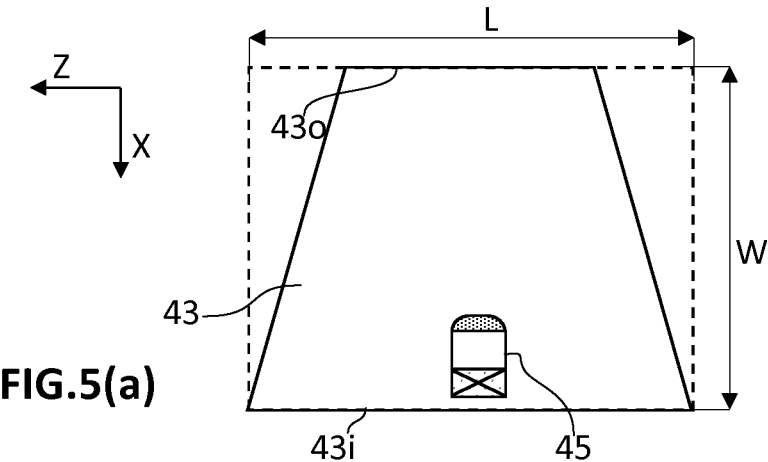
FIG. 5: shows an embodiment of croissant-shaped cuff electrode according to the present invention (a) stretched and (b) curled-up.
Figure 5B:
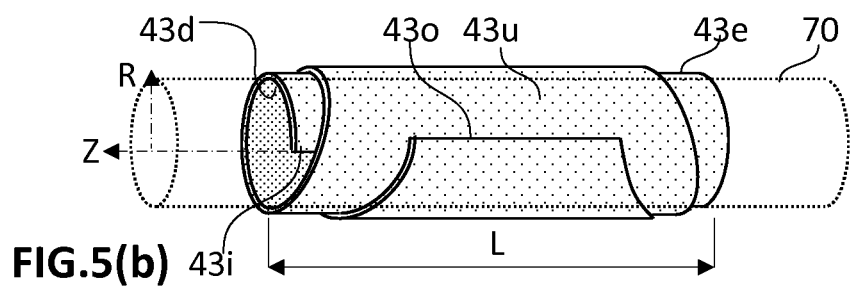
Figure 6A:
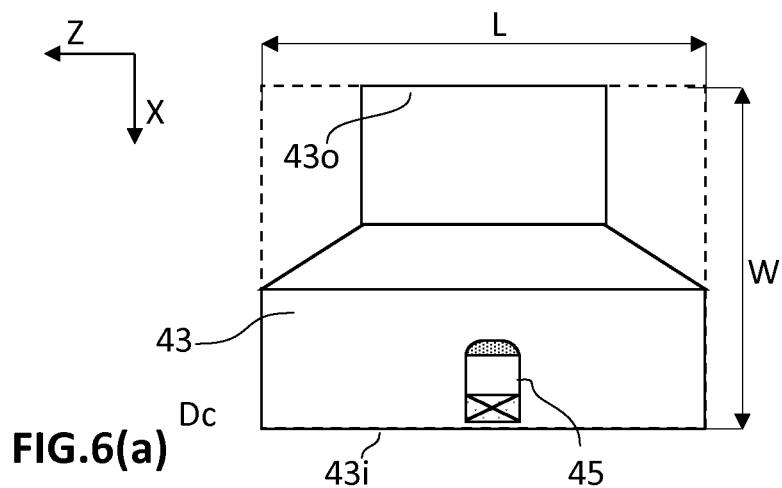
FIG. 6: shows an alternative embodiment of croissant-shaped cuff electrode according to the present invention (a) stretched and (b) curled-up.
Figure 6B:
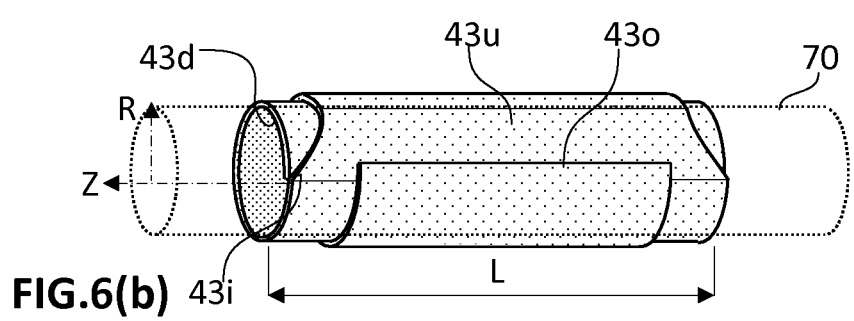

FIGS. 5 and 6 illustrate yet alternative embodiments wherein the insulating support sheet has a triangular (not shown) or trapezoidal geometry (cf. FIG. 5(a)), or two rectangles of different lengths along the longitudinal axis (Z), joined to one another either directly, forming a T (not shown), or joined by a trapezoidal portion (cf. FIG. § (a)). Upon rolling such insulating support sheets about the longitudinal axis (Z), a French croissant type of structure is obtained, wherein the edges of self-sizing cuff electrode are thinner, and thus softer, than a central portion thereof. A croissant type cuff electrode is preferably, but not exclusively, made as a self-sizing cuff electrode by creating a bias by pre-stretching an inner sheet of a multi-layered laminate as described above.

It is also possible to highlight the inner edge (43i), the outer edge (43o) or both inner and outer edges of the insulating support sheet to ensure that the surgeon positions the inner edge in contact with the tissue to be treated, and the outer edge remains on the outer side of the cuff electrode upon curling. The highlight can be a coloured area, a coloured line, an arrow, or other graphical or alpha-numerical indication applied at or adjacent to said inner and/or outer edge(s). This simple solution ensures that a self-sizing cuff electrode is not implanted the wrong way, with the risk that the one or more electrode contacts do not contact the tissue they are supposed to stimulate.

Figure 7A:
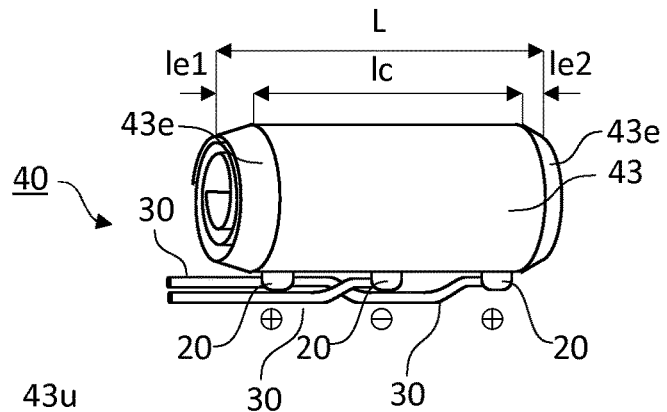
FIG. 7: shows a self-sizing cuff electrode (a) died view, (b) front view, (c) perspective view, (d)-(f) steps for coupling the self-sizing cuff electrode to a cylindrical tissue.
Figures 7B, 7C:
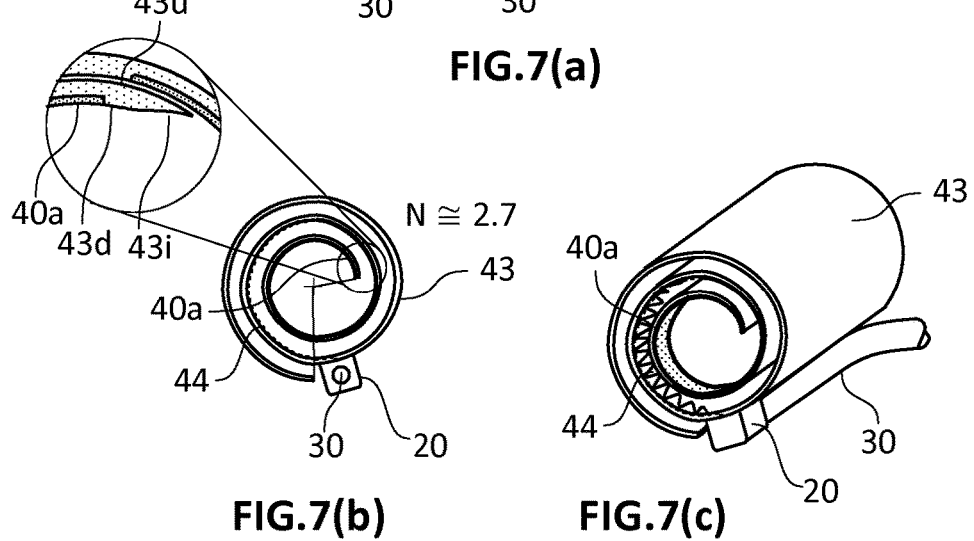
Figures 7D, 7E, 7F:
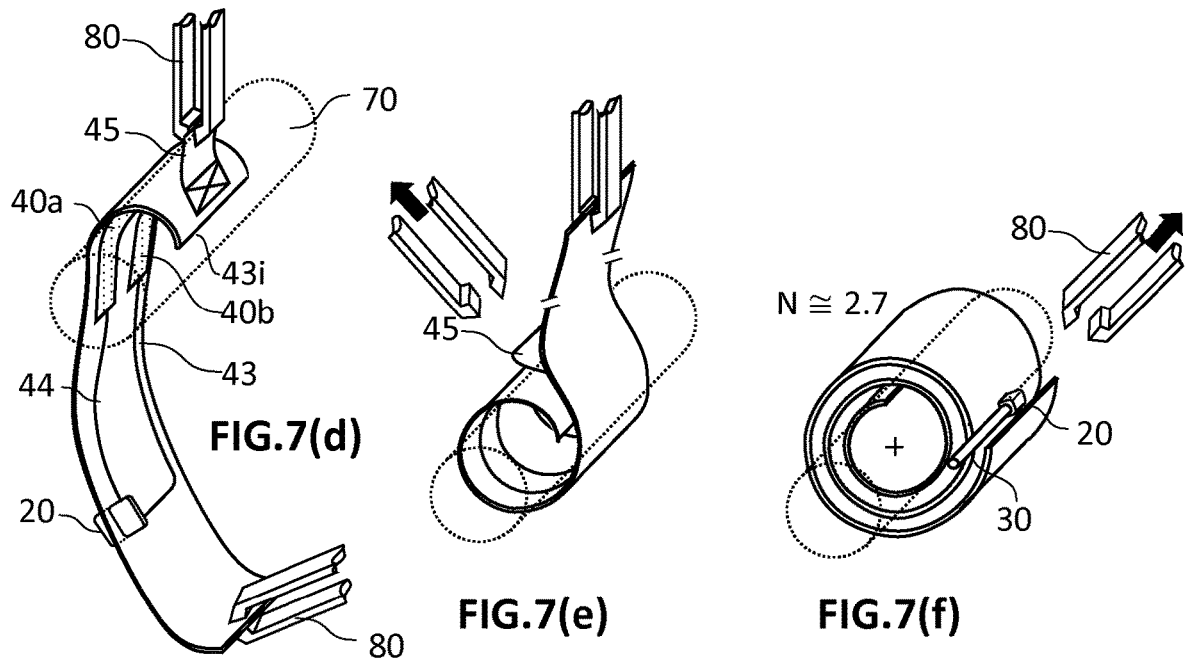

As shown in FIG. 7(a)-(f), a self-sizing cuff electrode/optrode generally surrounds a substantially cylindrical tissue with several loops. This has the double advantage of, on the one hand, safely securing the cuff electrode to the tissue and, on the other hand, to allow the self-sizing cuff electrode to vary the inner diameter (Dc) thereof to the size of a specific tissue and, more important, to adapt to size variations of said tissue with time (e.g., in case the tissue swells or, for children, the tissue grows). The higher the number (N) of loops the self-sizing cuff electrode surrounds the tissue with, the more secure is the coupling between the two. On the other hand, a high number (N), of loops increases the friction between adjacent loops, impairing the variations of the inner diameter (Dc) with tissue size variations and, at the same time increasing the bending stiffness of the cuff along the longitudinal axis (Z). As mentioned supra, it is preferred that the self-sizing cuff electrode surrounds a substantially cylindrical tissue with a number (N) of loops comprised between 1 and 3.5, preferably between 1.5 and 3.0, more preferably between 2.3 and 2.8. In FIGS. 7(b), 7(c), and 7(f), self-sizing cuff electrodes curled with a number N≅2.7 loops are illustrated. The number (N) of loops formed by a self-sizing cuff electrode depends on the actual diameter of the substantially cylindrical tissue which imposes the magnitude of the inner diameter (Dc), and on the width (W) of the inscribing rectangle, measured along the transverse axis (X). The level of bias obtained by pre-stretching the inner sheet prior to adhering it to the outer sheet determines the value of the inner diameter (Dc) the self-sizing cuff electrode spontaneously reaches at rest, i.e., free of any external constraints. In general, it is accepted that Dc at rest should be about 80 to 95%, preferably 85 to 90% of the diameter of the cylindrical tissue, so as to ensure a constant compressive coupling between the tissue and the electrode contacts, without injuring the tissue.

Because they must face the cylindrical tissue when implanted, the electrode contacts (40a-40c) generally reach close to the inner edge (43i) and are quite remote from the outer edge (cf. e.g., FIG. 7(d)). For this reason, an inner handling flap (45) is essential to the present invention to ensure preservation of the integrity of the electrode contacts and/or optical contacts. An outer handling flap (46) can be useful as it offers a comfortable handling grip close to the outer edge (43o), but little risk of damaging the cuff electrode arises from gripping the outer edge directly, as shown e.g., in FIGS. 7(d)&7(e)).

Split Cylinder Support Sheets

FIG. 4 illustrates split-cylinder cuff electrodes. A multi-layered laminate as described for self-sizing cuff electrodes can be used to create a self-curling bias. Alternatively, a single layer support sheet can be used too. The slit in FIG. 4(f) can be ligatured with stitches (43s) to secure the support sheet around the tissue. Alternatively, a sheath can be placed over the support sheet, with an opening off-set with respect to the slit of the cylinder. In some models, integrated locking means can be used to secure the inner and outer edges together. Finally, if the support sheet is biased to curl spontaneously, the bias can be strong enough to ensure maintenance of the support sheet over the tissue. A split-cylinder cuff support can be moulded directly into its final geometry. In this case a rigid or semi-rigid material can be used. Alternatively, it can also be made of a support sheet which is folded to form a split-cylinder as shown in FIG. 4. The cuff can be stitched together or the support sheet material can be set to this geometry, e.g., by cooling a thermoplastic material or setting a cross-linking thermoset or elastomer. The number (N) of loops is lower than in self-sizing cuff electrodes discussed supra, and can be comprised between 0.7 and 1.0, preferably between 0.8 and 1.0. For N<1, a cover flap (not shown) can be provided to cover the open slit remaining after implantation. Again, the number (N) of loops depends on the diameter of the cylindrical tissue, and on the width (W) of the support sheet measured along the transverse axis (X) when the support sheet is spread flat (or on a central cylindrical projection of the tubular support). The inner diameter (Dc) of split-cylinder cuff electrodes should be at least 97%, preferably between 100 to 110% of the diameter of the cylindrical tissue, to prevent injuries to the tissue caused by a generally more rigid support sheet than with self-sizing cuff electrodes discussed supra.

The electrode contacts (40a-40c) in a split-cylinder cuff electrode can reach close to both inner edge (43i) and outer edge (43o) extending over substantially the whole width (W) of the support sheet reaching a value of up to W measured along the transverse axis (X) (cf. e.g., FIG. 8(d)). For this reason, if an inner handling flap (45) is essential to the present invention to ensure preservation of the integrity of the electrode contacts (and/or optrodes), an outer handling flap (46) is highly preferred for the preservation of the electrode contacts at their ends adjacent to the outer edge (43o), as shown in FIGS. 8(d)&8(e)).

Inner Edge (43i), Outer Edge (43o)

The inner edge preferably forms a substantially straight line parallel to the longitudinal axis (Z). As shown in the inset of FIG. 7(b) the inner edge (43i) can be beveled so as to reduce the stress applied onto the tissue by a sharp inner edge. In all cases the inner edge (43i) must be in contact with the tissue (70)—alone for self-sizing cuff electrodes and with the outer edge for split-cylinder cuff electrodes. For this reason, it can be advantageous, in particular for self-sizing cuff electrodes, to highlight the inner edge (43i) with a distinctive colour or texture, to help the surgeon to easily and unambiguously distinguish the position of the inner edge.

The outer edge (43o) can also be substantially rectilinear. For example, split-cylinder cuff electrodes preferably have a support sheet having both inner and outer edges forming a substantially straight line, parallel to the longitudinal axis (Z). In an alternative embodiment, the outer edge (43o) can have a non-rectilinear geometry.

Figure 9B:
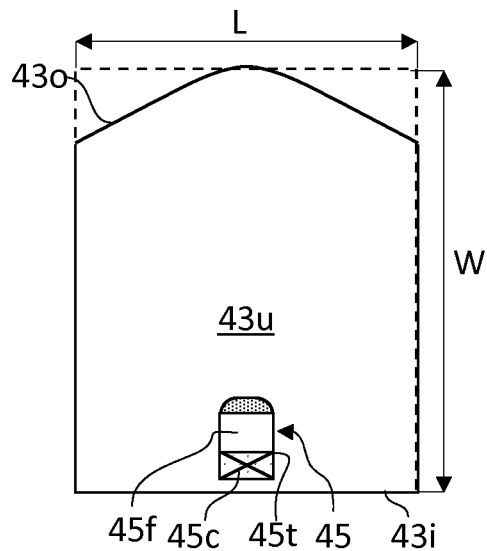
Figure 9C:
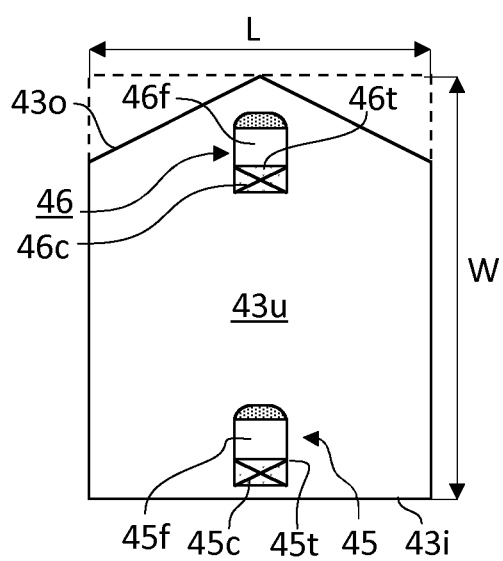
Figure 9D:
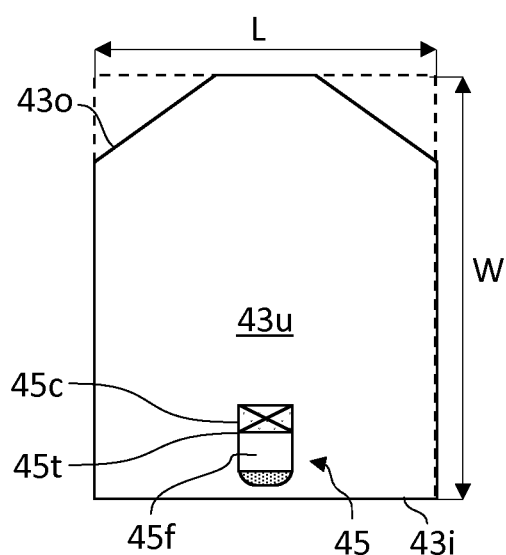

As illustrated in FIGS. 11(b) to 11(d), a central portion of the outer edge (43o) can be separated from the edge of the inscribing rectangle which is adjacent to the inner edge (43i) by the width (W) measured parallel to the transverse axis (X). The central portion is flanked by a first and second side portions, joining the central portion to the first and second lateral edges of the support sheet (43), respectively, the first and second lateral portions being separated from the edge of the inscribing rectangle which is adjacent to the inner edge (43i) by a distance shorter than the width (W). The central portion can be formed by a point forming an angle between the first and second side portions, as illustrated in FIG. 9(c). As illustrated in FIGS. 9(b) and 9(d), the central portion can alternatively form a straight or a curved segment of breadth measured parallel to the longitudinal axis (Z) lower than 80% of the longitudinal length (L), preferably comprised between 5 and 50% of L, more preferably between 10 and 33% of L. Such geometries have the advantage to offer a gripping zone for a second tweezer to hold the outer edge (43o) without risk of damaging any electrode contact (40a-40c), conductive track (44), or optrode (60). These geometries can replace or supplement the need of an outer handling flap (46).

Electrode Contacts (40a-c)

The cuff electrode of the present invention further comprises at least a first electrode contact (40a), generally at least a second electrode contact (40b) and, in a preferred embodiment, at least a third electrode contact (40c), each electrode contact being exposed at the inner surface (43d) of the support sheet, such as to be in electrically conductive contact with the tissue the cuff electrode is wrapped around. The electrode contacts are also remote from the outer surface forming the exterior of the cuff. The at least one contact electrode is separated from the adjacent lateral edge of the support sheet by a given distance. When the support sheet bears two electrode contacts (40a, 40b), they are separated from one another by a given distance. The various distances between electrode contacts and to the edges must be determined to confine the current within the section of tissue comprised between the first and second electrode contacts, and to minimize current losses, straying beyond the boundaries of the cuff electrode. Several factors are responsible for current losses. First, conductive body fluids penetrating between the support sheet and the tissue are responsible for some current losses.

Undesired tissue stimulation can be observed in bipolar cuff electrodes. They can be caused by so called virtual electrodes formed at a section of the tissue located beyond a lateral edge of the support sheet. A circuit is thus created between such virtual electrode and an electrode contact adjacent to the lateral edge. The probability for a tissue to be activated by a stimulating current at any point along the substantially cylindrical tissue is proportional to the second derivative of the voltage profile along the substantially cylindrical tissue (=along the longitudinal axis (Z)) and is characterized by the activating function. The value of the activation function is increased by sudden variations of the voltage profile and, conversely, is decreased in the absence of any such sudden variation. A virtual electrode can be formed beyond the lateral edges of a cuff electrode because there is a sudden variation of voltage at said lateral edges, between the support sheet and the conductive body fluids.

As shown in FIGS. 3(b), 4(b), 7(a), and 8(a), a cuff electrode according to the present invention may be tripolar, i.e., comprising three electrode contacts (40a-40c) (in FIGS. 7(a) and 8(a), the presence of the electrode contacts is indicated by the signs ⊕, θ). A tripolar cuff electrode can be advantageous over a bipolar cuff electrode (i.e., comprising two electrode contacts (40a, 40b)), in that the current is confined within the cuff, thus reducing current losses in the surrounding tissues and fluids. Tripolar cuff electrodes practically eliminate the formation of virtual electrodes discussed supra.

The electrode contacts (40a-40c) are made of a conductive material, which must be biocompatible and long-term stable in a physiological environment. Typically, gold, platinum, iridium, and alloys thereof can be used for the electrode contacts. As shown in FIGS. 3(b), 4(b), 7(d), and 8(d), the electrode contacts (40a, 40b) can be in the form of continuous stripes surrounding part or the whole of the circumference of the cylindrical tissue. The stripes extend parallel to the transverse axis (X). If the support sheet is wrapped around the substantially cylindrical tissue with a number (N) of loops larger than 1, the length of the electrode contact stripes needs not be as long as the width (W) of the support sheet, measured along the transverse direction (X). The length of the electrode contact stripes does not need to exceed the circumference of the substantially cylindrical cuff electrode of diameter, Dc, i.e. the conductive stripes need not be longer than π·Dc.

The electrode contacts can be printed or otherwise deposited (e.g., by physical vapour deposition (PVD) or by chemical vapour deposition (CVD)) onto the inner surface (43d) of the support sheet. This technique is advantageous in that the metal contacts do not stiffen the support sheet, which is particularly sensitive for self-sizing cuff electrodes and for split-cylinder cuff electrodes comprising a biased support sheet spontaneously curling. Another advantage is that the electrode contacts are over the inner surface (43d) of the support sheet, thus ensuring a physical contact of the electrode contacts with the cylindrical tissue. The geometry of the electrode contacts can also be controlled very easily.

Alternatively, the electrode contacts can be coupled to the support sheet as metal stripes or elements. They can be coupled to the inner surface (43d) of the support sheet by gluing or welding. Alternatively, and as illustrated in FIG. 4(a), metal stripes can be sandwiched between an inner sheet and an outer sheet, forming a laminate. Contact windows (43w) are provided in the inner sheet to expose the metal surfaces to the inner surface (43d). The electrode contacts thus formed are recessed from the inner surface (43d) by the thickness of the inner sheet. As described in U.S. Pat. No. 8,155,757, recessed electrode surfaces provide an advantage in that they facilitate better cross-sectional current distribution across a nerve as well as more uniform charge injection into the tissue being stimulated. As shown in FIG. 6 of U.S. Pat. No. 8,155,757, the geometry of the edges of the contact windows (43w) can also be optimized depending on the desired charge distribution. This embodiment, requiring inner and outer sheets is well suited for producing self-sizing cuff electrodes as discussed supra.

Because straight metal stripes cannot be stretched, thus impairing the advantage of self-sizing cuff electrodes of adapting to size variations of the tissue they are wrapped around, it can be advantageous instead of straight stripes to use stripes forming a serpentine, as shown as #40b & 40c in FIGS. 3(b) and 4(b). As an alternative to continuous electrode contact stripes, discrete electrode contact elements (not shown) can be used instead. The discrete electrode contact elements are preferably distributed in one or more rows extending parallel to the transverse axis (X) when the support sheet is deployed on a flat surface, at least along the portion of the inner surface forming the interior of the cuff. Discrete electrode contact elements can be advantageous over continuous electrode contact strips because they take full advantage of the flexibility of self-sizing support sheets. Additionally, they may be used to stimulate specific points of a tissue.

If the electrode contacts are formed by sandwiching a metal stripe between inner and outer sheets as discussed above with reference to FIG. 4(a), the geometry of the individual electrode contacts is defined by the geometry of the contact windows (43w). The geometry of each discrete electrode contact is not restricted by the present invention. A person of ordinary skill in the art knows how to select the electrode contacts configuration and dimensions best suited for a particular application.

From the Electrode Contacts (40a-40c) to the Corresponding Leads (30)

Energy pulses generated by the energy pulse generator located in the housing (50) are conveyed through the leads (30) and must be delivered to the electrode contacts (40a-40c) in the form of electrical energy. The electrode contacts (40a-40c) are exposed at the inner surface (43d) of the support sheet and electrically insulated from the outer surface (43u). The connection between the electrode contacts and the leads can be ensured by connecting pads (20) coupled to the outer surface of the support sheet. The connecting pads receive the one or more leads (30) and bring them in electrical communication with the corresponding electrode contacts. To this effect, the outer surface (43u) of the support sheet may comprise connecting windows (44w) allowing the formation of an electric communication between the electrode contacts (40a-c) and the connecting pads (20) coupled to the outer surface (cf. FIGS. 3(a)&4(a)).

If the connecting pads (20) are located in registry with the corresponding electrode contacts (40a-c), electrical communication between the leads and the electrode contact can be achieved directly though the connecting windows. If, on the other hand, the connecting pads are offset with respect to the electrode contacts, conductive tracks (44) can be used to bring in electrical communication the electrode contacts with the corresponding connecting pads. This is particularly the case with self-sizing cuff electrodes which can be wrapped with N=2 or more loops, whilst the electrode contacts should only be long enough to contact the perimeter of the cylindrical tissues (i.e., N=1). Conductive tracks (44) can be used to ensure electrical circuit continuity along the additional loops wherein the support sheet is not in contact with the cylindrical tissue. The conductive tracks can reach the outer surface through the connecting windows (44w).

In self-sizing cuff electrodes forming a tubular cuff made of N>1 loop, it is preferred that the connecting pads are coupled to a portion of the outer surface (43u) of the last loop, which forms an outer surface of the cuff. More preferably, the connecting pads are located as shown in FIGS. 7(b), 7(c), and 7(f) upstream and adjacent to the outer edge (43o) ending the last loop. In the present context, the term upstream refers to the winding direction starting from the interior of the cuff.

The conductive tracks can consist of a continuous conductive path bringing the electrode contacts (40a-c) in electric communication with the connecting pads through the connecting windows (44w). If the support sheet is made of a resilient material, the conductive tracks preferably form a serpentine which can be stretched longitudinally. Like the electrode contacts, as illustrated in FIGS. 3(a), 3(b), 4(a), and 4(b), the conductive tracks can be printed or deposited onto the inner surface (43d) of the support sheet. Alternatively, they can be sandwiched between an inner layer and an outer layer as illustrated in FIG. 4(a). Since the conductive tracks need not be in contact with any external tissue, no contact window (43w) is required in the inner layer to expose the conductive tracks. The conductive tracks must, however, lead to a connecting window (44w) to establish an electric contact with the connecting pads (20) coupled to the outer surface (43u).

In one embodiment, the energy pulse generator generates electrical pulses which are conducted to a connecting pad (20) coupled to the outer surface (43d) of the support sheet (43) by one or more conductive wires (30). As illustrated in FIG. 11(a), the connecting pad (20) comprises a wire receiving portion for receiving the one or more conductive wires (30). It also comprises one or more electrode coupling surfaces in electrical contact with corresponding electrode contacts (40a-40c) or with the one or more conductive tracks (44) electrically coupled to corresponding electrode contacts. The connecting pad (20) brings in electrical communication the one or more conductive wires (30) with corresponding electrode coupling surfaces or conductive tracks through the connecting windows (44w).

In an alternative embodiment, the energy pulse generator comprises a source of light emission and the lead (30) comprises optical fibres. Optical energy is transported to the connecting pads through the optical fibres. As illustrated in FIG. 11(b), the connecting pad comprises an optical fibre receiving portion and contains a circuit including a photovoltaic cell (20A) for transforming the optical energy transported by the optical fibre into electrical energy to feed the electrode contacts (40a-40c), in a manner similar to the one described supra in relation with an electric pulse generator. A connecting pad for photovoltaic IMD's suitable for use with an electrode cuff according to the present invention is described in detail in PCT/EP2017/071858.

Optical Contacts (60)

As illustrated in FIGS. 11(c) to 11(e), instead of, or additionally to electrode contacts (40a-40c), the support sheet can be provided with one or more optical contacts, also referred to as optrodes (60). An optical contact or optrode as defined herein can be either a light emitter or a light sensor, or both. In some applications, stimulation of a tissue by light emission is mainly due to localized heating of the tissue. For such applications, it is preferred that the light directed by the optical contact be in the infrared range, preferably in the range of 750 to 3000 nm, more preferably of 1200 to 1800 nm. The cuff optrode of the present invention, however, can be used with light beams (60B) of any wavelength.

As illustrated in FIGS. 11(c) to 11(e), an optical contact can be the end of an optical fibre, which is either beveled or coupled to a lens, mirror, or other micro-optic device for directing and focusing a light beam (60B) towards a precise area of the tissue to be treated. The fibre optic can be coupled directly to the housing (50) and to the light pulse generator housed therein. Alternatively, a light emitting device located on an outer surface of the cuff can be electrically powered by the energy pulse generator located in the housing, and the optical fibre can be coupled to said light emitting device for guiding the light towards the tissue.

The optical contact (60) can also be one or more LEDs, VCSELs or other laser diodes which are mounted on the insulating sheet such as to be in direct optical contact with the tissue around which the cuff is wrapped. If the insulating sheet is transparent to the light wavelength emitted by the optical contact, then the light can be transmitted through the thickness of insulating sheet separating the optical contact from the inner surface (43d) of the insulating sheet. If the insulating sheet is not transparent enough for an efficient transmission of the light energy, then a window (43w) can be provided at the inner surface of the insulating sheet to expose the optical contact.

The LED, VCSEL or other laser diode can be fed with electrical current in the same way as described with respect to the electrode contacts (40a-40c).

Various Cuff Electrode/Optrode Configurations

FIG. 11 illustrates various configurations of a cuff electrode/optrode according to the present invention. FIG. 11(a) illustrates a cuff electrode according to the present invention as discussed in detail supra. It comprises a lead (30) transporting energy to a connecting pad (20) whence the energy is conveyed to a first and second electrode contacts (40a, 40b). The energy can be transported from the energy pulse generator located in the housing (50) (not shown) in the form of electric energy. In this case, the connecting pad (20) is simply a contact point between the lead (30) and the conductive tracks (44). Alternatively, the energy can be transported in the form of light through a fibre optic (30) and the connecting pad comprises a photovoltaic cell (20P) able to transform the light energy into electric energy, which is fed to the first and second electrode contacts, as shown in FIG. 11(b).

The connecting pad may comprise a electronic amplifier for amplifying signals of potential variations between the first and second electrodes, representative of an activity of the tissue wrapped by the cuff electrode. The cuff electrode can thus be used in a sensing mode, for detecting activity signals of a tissue. The electronic amplifier can be located in the housing (50) instead of in the connecting pad. In this embodiment, the cuff electrode can also be used in a sensing mode, for detecting activity signals of a tissue.

FIG. 11(c) illustrates a cuff optrode according to the present invention. In this embodiment, a fibre optic (30) coupled to a light pulse generator located in a housing (50) (not shown) is coupled to the insulating sheet (43) and is configured for driving a light beam (60B) to a precise area of the tissue to be treated. As discussed above, the end of the fibre optic can be beveled or coupled to a lens; mirror, or other micro-optic device, adapted for guiding the light beam where desired.

FIG. 11(d) illustrates a cuff optrode very similar to the one of FIG. 11(c), further comprising a sensing optrode (60S) for sensing the light scattered, reflected or transmitted after interaction of the beam (60B) with the tissue (70). The optical signal thus sensed can be transmitted to the housing, either in the form of light, or of an electric signal, provided the sensing optrode is capable of transforming a light signal into an electric signal (e.g., with a photovoltaic cell).

FIG. 11(e) illustrates a cuff electrode/optrode very similar to the cuff optrode of FIG. 11(c), further comprising a first and second electrode contacts (40a, 40b) suitable for sensing activity signals of a tissue as discussed above, electrically coupled to an electronic amplifier (20A) provided either in the housing (50) or in the connecting pad (20) (cf. FIG. 11(e)).

Process for Implanting a Cuff Electrode

The implantable cuff electrode of the present invention renders implantation thereof much easier and safer than hitherto made possible with prior art cuff electrodes. An implantable cuff electrode of the present invention can be implanted around a tissue (70) of substantially cylindrical geometry by a method comprising the following steps:

In case the inner handling flap (45) is not accessible (e.g., in a self-sizing cuff electrode with e.g., N>2), opening the cuff by gripping the outer edge (43o) or, if available, an outer handling flap (46), until providing access to the inner handling flap (45), gripping the free portion (45f) of the inner handling flap (45) of a cuff electrode according to the present invention with a tweezer (80), bringing a portion of the inner surface (43u) contiguous to the inner edge (43i) in contact with the tissue, while holding the inner handling flap (45) with the tweezer (80), and wrapping the support sheet (43) around the tissue and, after 0.8 to 1.5 loops, releasing the grip by the tweezer on the inner handling flap, FIGS. 7(d) to 7(f) illustrates the foregoing steps with a self-sizing cuff electrode. It can be seen that it does not comprise any outer handling flap (46). Consequently, while a first tweezer (80) grips the inner handling flap (45) thus preserving the integrity of the electrode contacts and/or conductive tracks, a second tweezer can grip the outer edge (43o). This is not a major issue for self-sizing cuff electrodes because the electrode contacts and conductive tracks (44) are generally remote from the outer edge (43o) and the risk of damaging them with tweezers is quite low. An outer handling flap (46) is nonetheless advantageous as it provides a firm grip at a central portion adjacent to the outer edge (43o). The wrapping step can comprise forming N>1 loop, preferably between 1.5 and 3.0 loops.

FIG. 8(d) to 8(f) illustrates the foregoing steps with a split-cylinder cuff. It can be seen that, an inner handling flap (45) remains useful for gripping one end portion of the support sheet (43) adjacent to the inner edge (43i), and an outer handling flap (46) becomes very useful for gripping an opposite end portion adjacent to the outer edge (43o) reducing the risk of damaging any of an electrode contact, conductive track, or optrode. Here the wrapping step can comprise forming N=0.8 to 1 loop. The slit formed between the inner and outer edges (43i, 43o) can optionally be ligatured with stitches (43s).

Advantages of the Present Invention

The provision of an inner handling flap (45) at a portion of the outer surface (43u) which is adjacent to the inner edge (43i) greatly facilitates and accelerates the implantation of a cuff electrode with a firm grip at a central portion adjacent to the inner edge (43i), substantially reducing the risk of damaging any component of the cuff electrode including an electrode contact (40a-40c), a conductive track (44), and/or an optrode (60). If the cuff electrode comprises no outer handling flap (46), the position of the inner handling flap (45) is a clear indication to a surgeon of the position of the inner edge (43i) and assists the surgeon in positioning the support sheet with the correct orientation for a successful implantation. The use of different colour codes for the inner and outer handling flaps or for the inner and outer edges is also advantageous to ensure a proper implantation of the cuff electrode, with the electrode contacts or optrode contacts facing the tissue to be treated.

The provision of an outer handling flap (46) further increases the easy handling of the cuff electrode obtained with the inner handling flap (45). As shown in FIG. 8(d)-8(f), an inner and an outer handling flaps (45, 46) renders the implantation of a split cylinder cuff electrode fool-proof in that there is one orientation only allowed by the flaps, and the tweezers never get close to any electrode contact (40a-40c). Inner and outer handling flaps also provide a firm grip at central portions adjacent to the inner and outer edges, respectively.

All the foregoing advantages are obtained with no substantial increase of the production costs of the cuff electrode.

| Ref | Feature |
|---|---|
| 20 | Connecting pad, connecting electrode contact and/or optrode to lead (30) |
| 20A | Electronic amplifier |
| 20P | Photovoltaic cell |
| 30 | Lead for energy transfer between the cuff electrode and/or optrode and the housing (50) |
| 40 | Cuff electrode and/or optrode |
| 40a | Electrode contact |
| 40b | Electrode contact |
| 40c | Electrode contact |
| 43 | Support sheet |
| 43d | Inner surface of the support sheet |
| 43i | Inner edge of the support sheet |
| 43o | Outer edge of the support sheet |
| 43s | Stitches |
| 43u | Outer surface of the support sheet |
| 43w | Contact window in the inner surface for exposing electrode contact |
| 44 | Track coupling an electrode contact to a connexion (20) |
| 44w | Window in the support sheet between a track (44) and a connexion (20) |
| 45 | Inner handling flap |
| 45c | Coupled portion of the inner handling flap |
| 45f | Free portion of the inner handling flap |
| 45t | Transition line of inner handling flap |
| 46 | Outer handling flap |
| 46c | Coupled portion of the outer handling flap |
| 46f | Free portion of the outer handling flap |
| 46t | Transition line of outer handling flap |
| 50 | Housing containing an energy pulse generator |
| 60 | Optrode |
| 70 | Substantially cylindrical tissue, such as a nerve |
| 80 | Tweezer |
| 431 | Inner sheet forming a support sheet laminate |
| 432 | Outer sheet forming a support sheet laminate |
| b | Breadth along Z of the inner handling flap |
| Dc | Cuff electrode and/or optrode inner diameter |
| he | Distance of the free end of the inner handling flap to the inner edge |
| hf | Length along X of the free portion of the inner handling flap |
| hs | Distance along X of the free portion of the inner handling flap to the inner edge |
| L | Length along Z of the inscribing rectangle which the support sheet is inscribed in |
| W | Width along X of the inscribing rectangle which the support sheet is inscribed in |
| X | Transverse axis |
| Z | Longitudinal axis |

The invention claimed is:

1. An implantable cuff electrode and/or optrode adapted to encircle substantially cylindrical body tissue, and selected among a self-sizing cuff and a split-cylinder cuff, said implantable cuff electrode and/or optrode comprising:
   a support sheet which is non-conductive, and
      having an inner surface and an outer surface separated from the inner surface by a thickness,
      having a perimeter inscribed in an inscribing rectangle of length (L) measured parallel to a longitudinal axis (Z), and of width (W) measured parallel to a transverse axis (X) normal to the longitudinal axis (Z), the perimeter being defined by an inner edge and an outer edge extending along the length (L) of the inscribing rectangle, and by a first and second lateral edges extending along the width (W) of the inscribing rectangle, wherein
      the support sheet is rolled about the longitudinal axis, forming a cuff of substantially cylindrical geometry extending over the length, along the longitudinal axis, such that at least a portion of the inner surface forms an interior of the cuff, and such that at least a portion of the outer surface forms an exterior of the cuff,
   at least a first energy transfer unit including an electrode contact or an optical contact, which is exposed at the inner surface of the cuff,
   wherein, an inner handling flap is provided which comprises
      a coupled end belonging to a coupled portion which is fixed to a portion of the outer surface of the support sheet which is adjacent to the inner edge, and
      a free end, opposite the coupled end, belonging to a free portion adjacent to the coupled portion and separated therefrom by a transition line, said free portion being loose from the outer surface of the support sheet and wherein the coupled end of the inner handling flap is adjacent to the inner edge and the free end faces towards the outer edge of the support sheet when the support sheet is spread flat.

2. The implantable cuff electrode and/or optrode according to claim 1,
   wherein the transition line is parallel to the longitudinal axis (Z) and wherein,
      the inner handling flap has a breadth measured parallel to the longitudinal axis comprised between 20 and 50% of the support sheet length, and/or
      the free portion of the inner handling flap has a length (hf) measured parallel to the transverse axis (X) comprised between 3 and 10 mm, and/or
      the transition line is separated from the inner edge by a distance (hs) measured parallel to the transverse axis (X) of not more than 6 mm.

3. The implantable cuff electrode and/or optrode according to claim 1,
   wherein the transition line extends along the longitudinal axis (Z) and is separated from the inner edge by a distance (hs) measured parallel to the transverse axis of not more than 4 mm.

4. The implantable cuff electrode and/or optrode according to claim 1, wherein the implantable cuff electrode comprises first and second electrode contacts to form a bipolar electrode.

5. The implantable cuff electrode and/or optrode according to claim 1, wherein the support sheet is formed of an outer sheet comprising the outer surface, adhered to an inner sheet comprising the inner surface, and wherein said inner sheet is made of a resilient material and is resiliently pre-strained along the transverse axis (X), to create a bias suitable for self-curling the support sheet about the longitudinal axis (Z), to resiliently form a substantially cylindrical cuff of inner diameter (Dc).

6. The implantable cuff electrode and/or optrode according to claim 1, wherein the implantable cuff electrode and/or optrode forms a self-sizing cuff and wherein the support sheet has a bias and inner and outer widths (W), such that the support sheet self-curls into the substantially cylindrical cuff of inner diameter (Dc), with N loops, with N being comprised between 1.1 and 3.5, wherein
   the interior of the cuff is formed by the inner edge together with the at least portion of the inner surface, and the exterior of the cuff is formed by the outer edge together with the at least portion of the outer surface, and
   the at least first energy transfer unit is closer to the inner edge than to the outer edge.

7. The implantable cuff electrode and/or optrode according to claim 1, wherein the implantable cuff electrode and/or optrode forms a split-cylinder cuff and wherein the support sheet has a bias and inner and outer widths (W), such that the support sheet self-curls into the substantially cylindrical cuff of inner diameter (Dc), with N loops, with N being comprised between 0.8 and 1.0, and wherein the inner edge and the outer edge face each other, and wherein the at least first energy transfer unit has a length of up to W.

8. The implantable cuff electrode and/or optrode according to claim 1, comprising a first electrode contact and a second electrode contact, and wherein the first and second electrode contacts are in the form of,
- continuous strips extending parallel to the transverse axis (X) when the support sheet is deployed on a flat surface, at least along the portion of the inner surface forming the interior of the cuff, or
- discrete electrode contact elements distributed parallel to the transverse axis (X) when the support sheet is deployed on a flat surface, at least along the portion of the inner surface forming the interior of the cuff.

9. The implantable cuff electrode and/or optrode according to claim 1, wherein an outer handling flap is provided in a portion of the outer surface contiguous to the outer edge, which comprises
- a coupled end belonging to a coupled portion which is fixed to a portion of the outer surface of the support sheet which is adjacent and contiguous to the outer edge, and
- a free end, opposite the coupled end, and adjacent to the outer edge of the support sheet, said free end belonging to a free portion which is loose from the outer surface of the support sheet.

10. The implantable cuff electrode and/or optrode according to claim 1, wherein a central portion of the outer edge is separated from the edge of the inscribing rectangle which is adjacent to the inner edge by the width (W) measured parallel to the transverse axis (X), and is flanked by a first and second side portions, joining the central portion to the first and second lateral edges of the support sheet, respectively, the first and second lateral portions being separated from the inner edge by a distance shorter than the width (W), and wherein the central portion is formed either by,
- a point forming an angle between the first and second side portions, or
- a straight or curved segment of breadth measured parallel to the longitudinal axis (Z) lower than 80% of the longitudinal length (L).

11. The implantable cuff electrode and/or optrode according to claim 1, wherein the inner edge and/or the outer edge of the insulating support sheet are highlighted comprising one or more of a coloured area, a coloured line, an arrow, or other graphical or alpha-numerical indication applied at or adjacent to said inner and/or outer edge(s).

12. The implantable cuff electrode and/or optrode according to claim 1, wherein the inner handling flap comprises a colour code.

13. The implantable cuff electrode and/or optrode according to claim 12, comprising an outer handling flap according to claim 9, comprising a colour code different from the colour code of the inner handling flap.

14. A method for implanting a cuff electrode and/or optrode around a tissue of substantially cylindrical geometry, the method comprising:
(a) providing an implantable cuff electrode and/or optrode according to claim 1,
(b) gripping the free portion of the inner handling flap with a tweezer,
(c) bringing a portion of the inner surface contiguous to the inner edge in contact with the tissue, while holding the inner handling flap with the tweezer, and
(d) wrapping the support sheet around the tissue and, after 0.8 to 1.5 loops, releasing the grip by the tweezer on the inner handling flap.

15. The method according to claim 14, wherein the wrapping the support sheet is performed with a second tweezer gripping either the outer edge of the support sheet or a free end of an outer handling flap, and releasing and removing the tweezer once the outer edge is in an implanted position.

16. The method according to claim 14, wherein the cuff electrode is either,
- a self-sizing cuff electrode and the wrapping step comprises forming N>1 loop, or
- a split cylinder cuff electrode and the wrapping step comprising forming N=0.8 to 1 loop and ligaturing the slit formed between the inner and outer edges with stitches.

* * * * *